United States Patent
Tai et al.

(10) Patent No.: US 10,240,689 B2
(45) Date of Patent: Mar. 26, 2019

(54) DIAPHRAGM CHECK VALVES AND METHODS OF MANUFACTURE THEREOF

(71) Applicant: MiniPumps, LLC, Pasadena, CA (US)

(72) Inventors: Yu-Chong Tai, Pasadena, CA (US); Po-Ying Li, Monrovia, CA (US); Fukang Jiang, Arcadia, CA (US); Changlin Pang, Temple City, CA (US); Natasha Yvette Bouey, Pasadena, CA (US); Man Ting Chou, Temple City, CA (US); Atoosa Lotfi, Valencia, CA (US)

(73) Assignee: MINIPUMPS, LLC, Pasadena, CA (US)

( * ) Notice: Subject to any disclaimer, the term of this patent is extended or adjusted under 35 U.S.C. 154(b) by 0 days.

(21) Appl. No.: 15/805,501

(22) Filed: Nov. 7, 2017

(65) Prior Publication Data
US 2018/0080578 A1    Mar. 22, 2018

Related U.S. Application Data

(63) Continuation-in-part of application No. 14/153,662, filed on Jan. 13, 2014, now Pat. No. 9,845,895.
(Continued)

(51) Int. Cl.
| F16K 15/14 | (2006.01) |
| F16K 99/00 | (2006.01) |
| B29C 70/76 | (2006.01) |
| A61M 39/24 | (2006.01) |
| B29L 31/00 | (2006.01) |
| B29C 45/14 | (2006.01) |

(Continued)

(52) U.S. Cl.
CPC ......... *F16K 99/0057* (2013.01); *A61M 39/24* (2013.01); *B29C 70/766* (2013.01); *F16K 15/145* (2013.01); *F16K 15/147* (2013.01); *F16K 99/0015* (2013.01); *A61M 2039/2426* (2013.01); *B29C 39/10* (2013.01); *B29C 41/20* (2013.01); *B29C 45/14598* (2013.01); *B29L 2031/753* (2013.01); *B29L 2031/756* (2013.01); *F16K 2099/0073* (2013.01); *F16K 2099/0078* (2013.01); *F16K 2099/0086* (2013.01); *Y10T 137/0497* (2015.04); *Y10T 137/7895* (2015.04)

(58) Field of Classification Search
CPC ......... F16K 99/0015; F16K 2099/0073; F16K 2009/0086; F16K 15/145; F16K 99/0057; F16K 15/14; F16K 9/0057; A61M 2039/2426; Y10T 137/7895
See application file for complete search history.

(56) References Cited

U.S. PATENT DOCUMENTS

| 2,417,968 A | * | 3/1947 | Browne | ............... F16K 15/147 |
| | | | | 137/850 |
| 3,525,357 A | * | 8/1970 | Koreski | .................. F04B 43/08 |
| | | | | 137/512.15 |

(Continued)

*Primary Examiner* — P. MacAde Nichols
(74) *Attorney, Agent, or Firm* — Morgan, Lewis & Bockius LLP

(57) ABSTRACT

Microscale valves for use in, e.g., micropump devices, may be formed of a slitted diaphragm bonded o the interior of a valve tube. A bump in the diaphragm and/or a backward-leakage stopper may increase the breakdown pressure of the valve. A push-rod may be used to pre-load the valve membrane to thereby increase the cracking pressure.

22 Claims, 30 Drawing Sheets

FLOW DIRECTION

Related U.S. Application Data

(60) Provisional application No. 61/751,645, filed on Jan. 11, 2013, provisional application No. 61/806,213, filed on Mar. 28, 2013.

(51) Int. Cl.
  *B29C 39/10* (2006.01)
  *B29C 41/20* (2006.01)

(56) References Cited

U.S. PATENT DOCUMENTS

| | | | |
|---|---|---|---|
| 5,010,925 A * | 4/1991 | Atkinson | F16K 15/147 137/846 |
| 7,721,763 B2 * | 5/2010 | Choksi | F16K 15/144 137/515.5 |
| 7,997,463 B2 * | 8/2011 | Quinn | B05C 17/00516 137/844 |

* cited by examiner

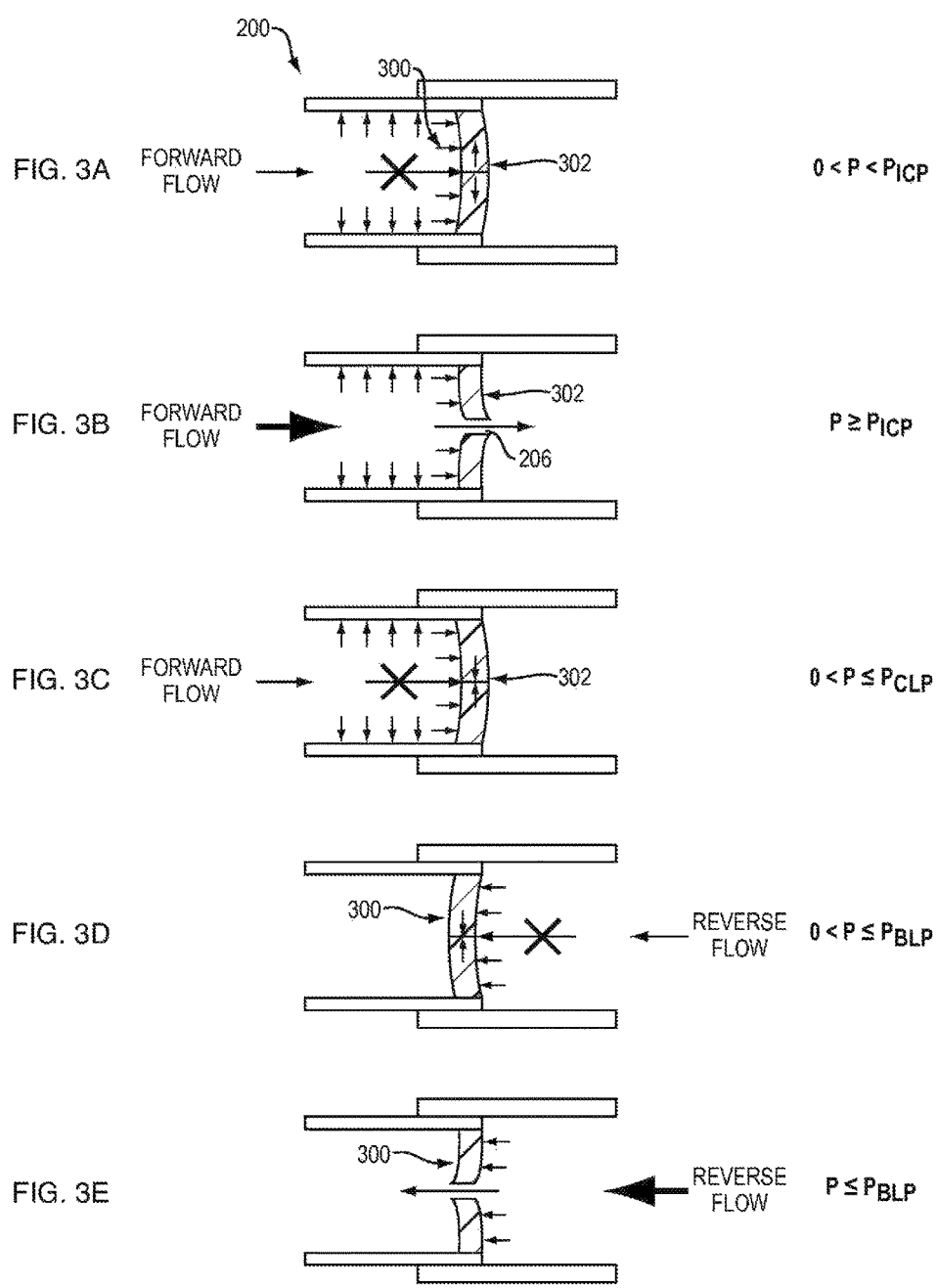

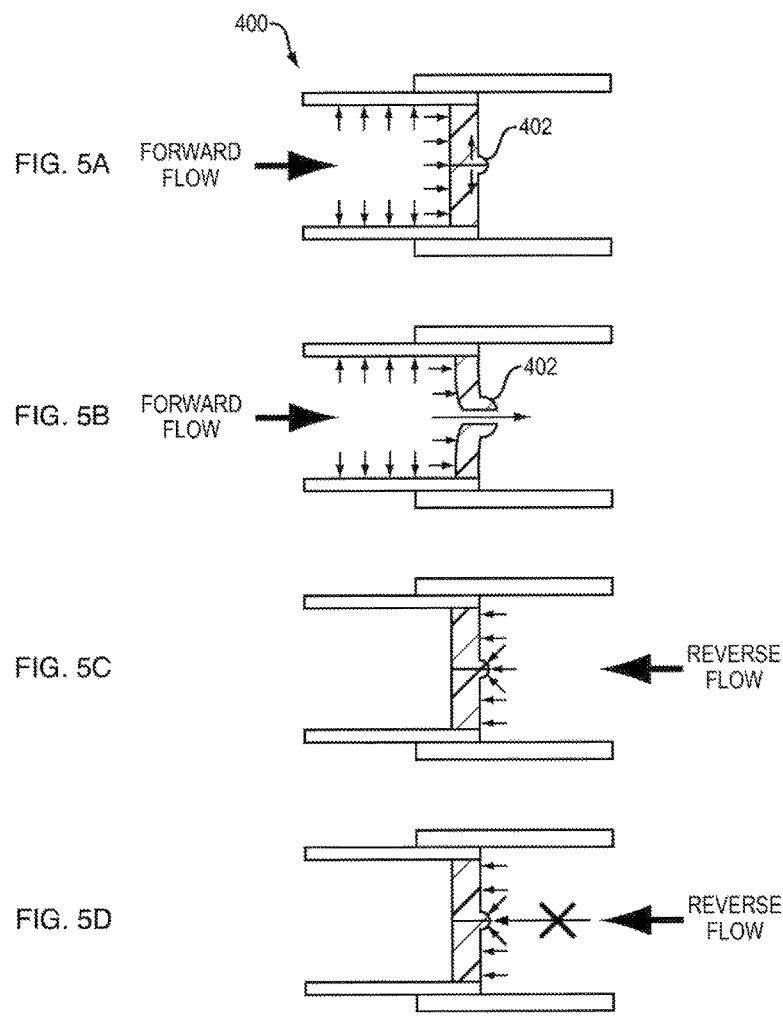

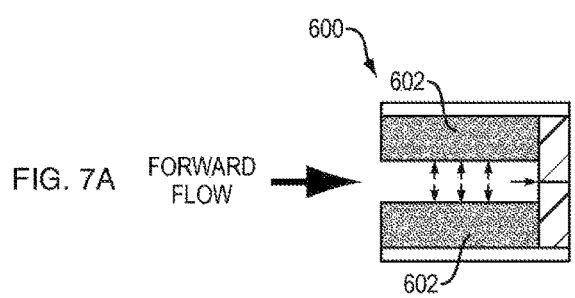
FIG. 7A  FORWARD FLOW
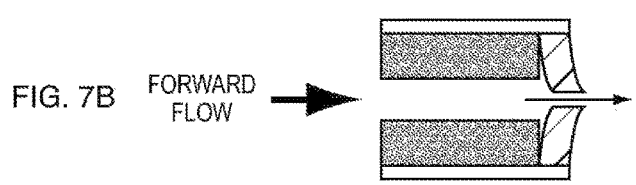
FIG. 7B  FORWARD FLOW
FIG. 7C  REVERSE FLOW
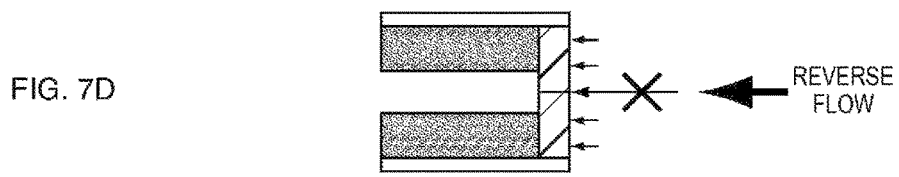
FIG. 7D  REVERSE FLOW

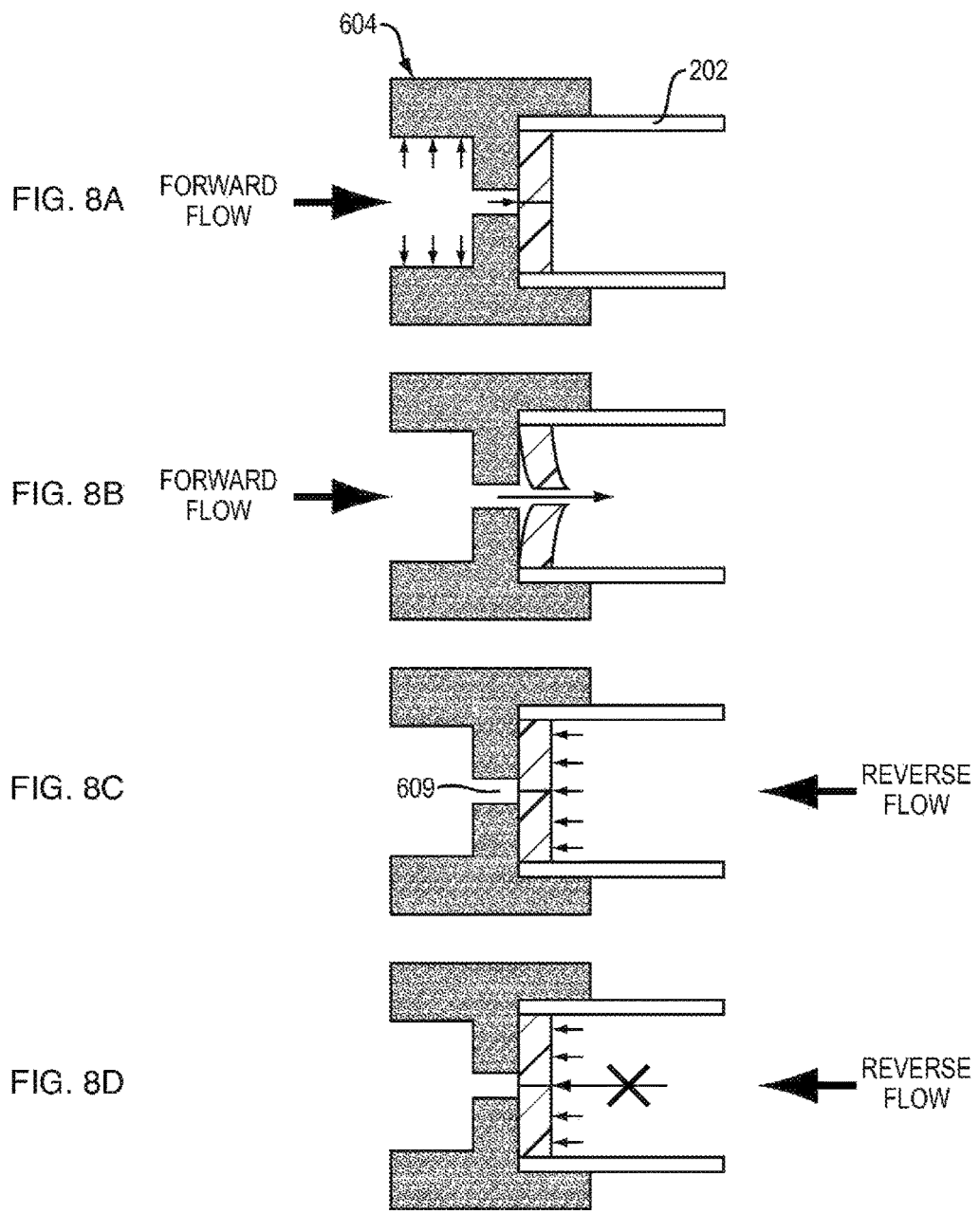

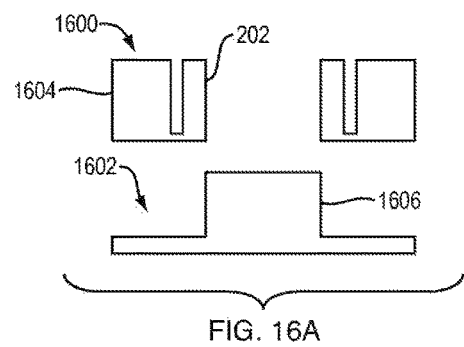
FIG. 16A
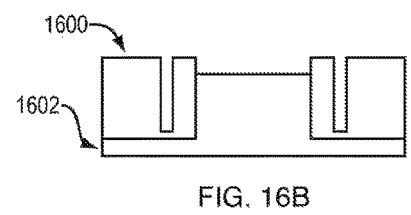
FIG. 16B
FIG. 16C
FIG. 16D
FIG. 16E
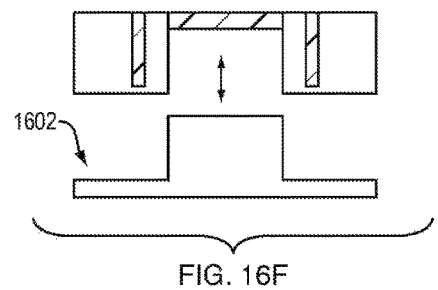
FIG. 16F
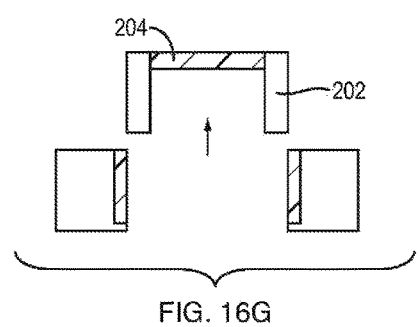
FIG. 16G
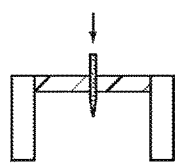
FIG. 16H
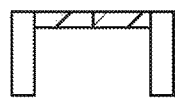
FIG. 16I

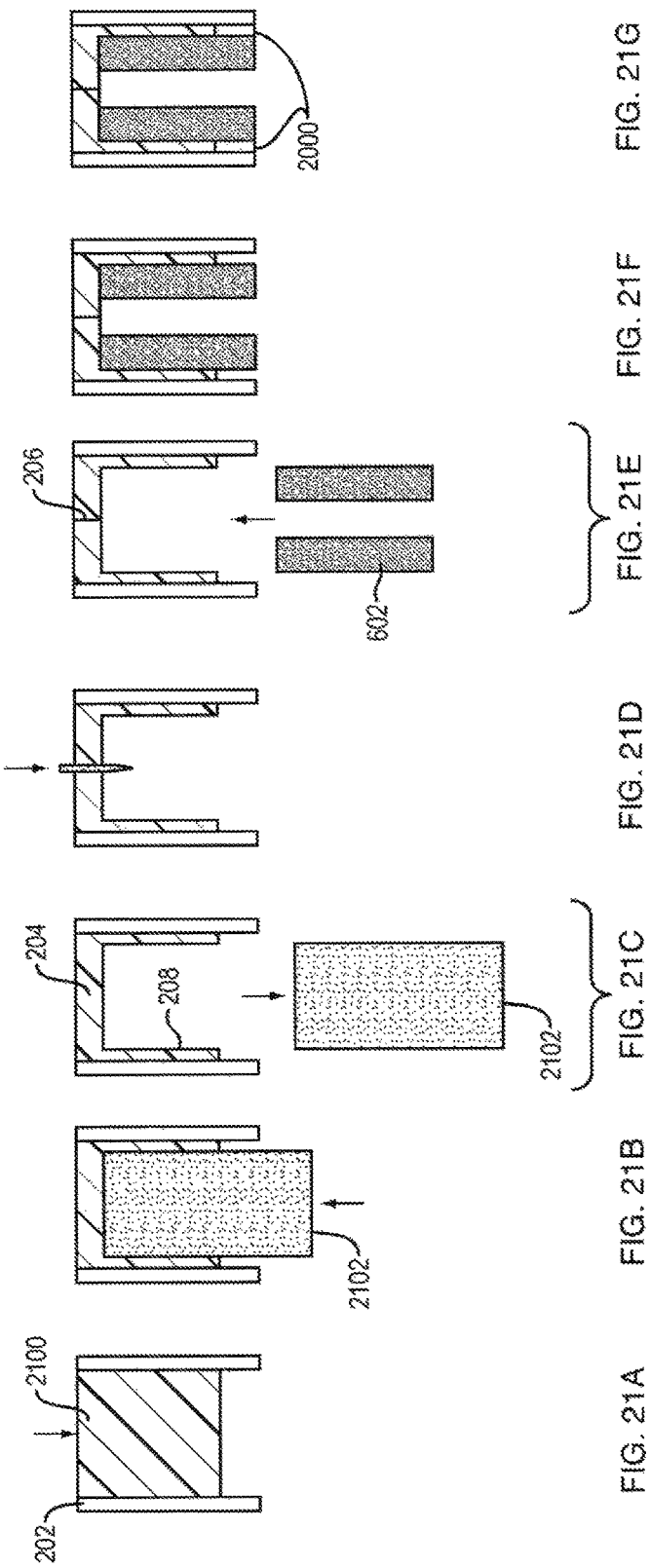

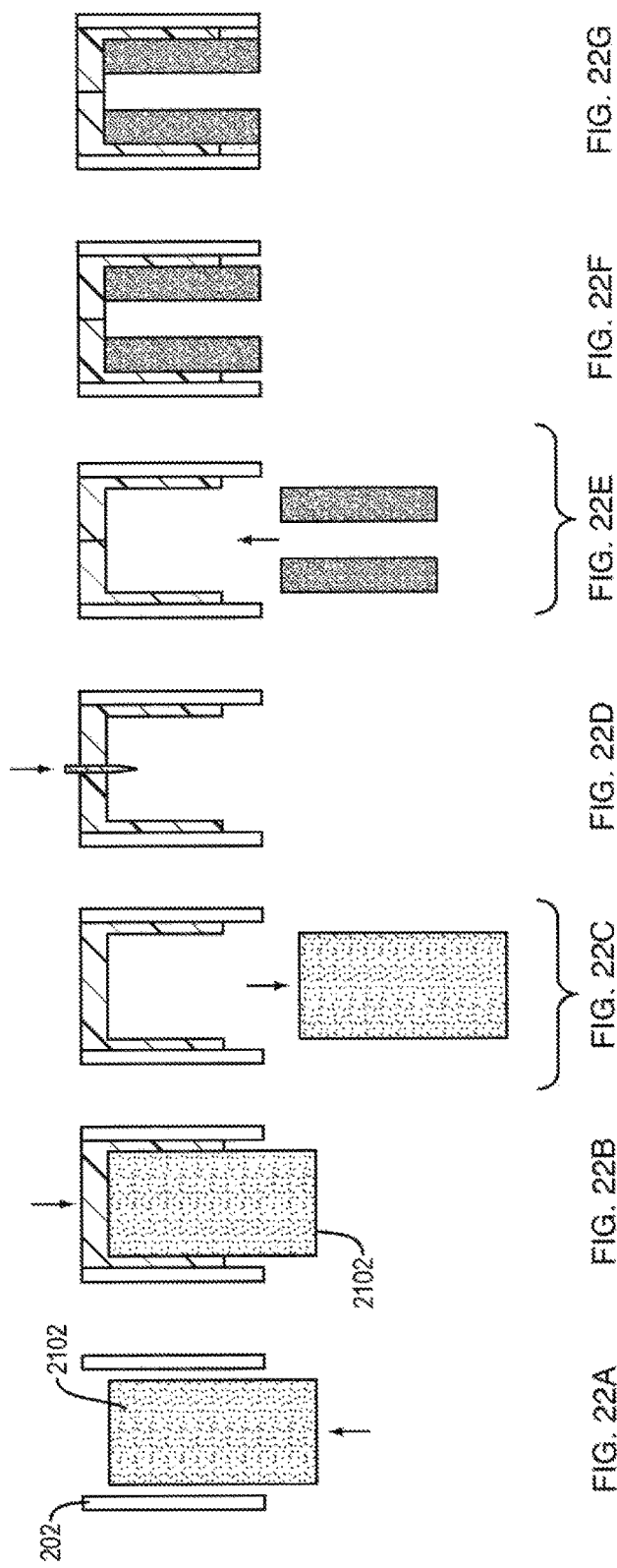

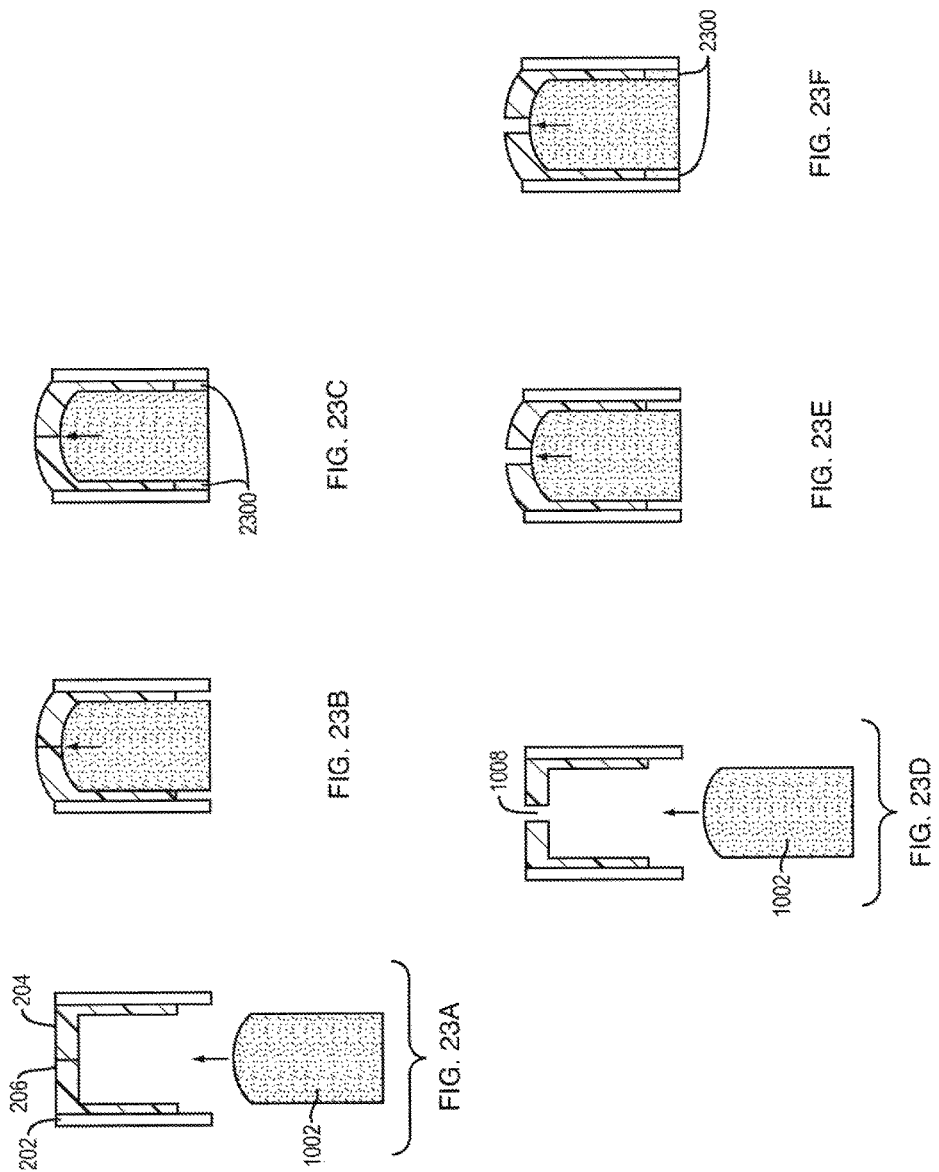

DIAPHRAGM CHECK VALVES AND METHODS OF MANUFACTURE THEREOF

CROSS-REFERENCE TO RELATED APPLICATION

This application is a continuation-in-part of U.S. patent application Ser. No. 14/153,662 (filed on Jan. 13, 2014), and also claims priority to and the benefit of U.S. Provisional Patent Application Nos. 61/751,645 (filed on Jan. 11, 2013) and 61/806,213 (filed on Mar. 28, 2013). The foregoing applications are incorporated herein by reference in their entireties.

TECHNICAL FIELD

The present invention relates to check valves and methods for their manufacture, and more particularly to microscale valves for use, e.g., in microfluidic devices such as small, implantable drug-delivery devices.

BACKGROUND

The need for ever-smaller pumping devices, particularly in the medical microdevice industry, continues to grow. As a result, the need for increasingly small operational pump components, such as check valves, is growing as well, challenging the limits of conventional manufacturing processes. The smallest commonly available check valves have dimensions in the range of 2-10 mm—too large for convenient integration into implantable micropumps with total dimensions in the range of 5-15 mm, as are desirable, e.g., for implantation into small organs such as the eye. Valves less than 1 or 2 mm in size, on the other hand, are difficult to fabricate using conventional technologies.

Part of the challenge in scaling down check valves lies in the complexity of traditional macro-size valve structures. A ball valve, for example, may include a ball, a spring, a rubber valve seal, and a housing fixture. The smoother the surfaces are and the closer the ball is to having perfect spherical shape, the better will be the contact between ball and valve seal, which defines the leakage rate and flow performance of the valve. At small scales, however, surface roughness and shape are difficult to control, and manufacture is, moreover, prone to misalignments of components (e.g., due to crimping of the outer housing). Consequently, it is hard to scale ball valves down in size while retaining proper function and performance. Similarly, silicone valves (e.g., duckbill valves) produced with conventional molding techniques tend to be unreliable (e.g., exhibiting leakage and large production variations) when scaled down to submillimeter dimensions. Yet, accurate, repeatable, and reliable flow/pressure performance is critical for many applications, such as drug delivery, where inaccuracies in the flow rate translate into potentially harmful or even fatal under- or overdosing.

A further challenge in the design of microscale check valves is the desired lifetime of the device. A microscale medical device usually requires an operating lifetime of two to ten years; this is especially true for implantable microscale drug-delivery pump systems. However, microscale check valves are prone to stiction or obstruction caused by microscopic particles, tissue growth, or drug sedimentation; indeed, conventional valve designs often need to balance a trade-off between good valve sealing in the closed state and a sufficiently open fluid path to avoid clogging when the valve is open. If obstructions in the valve occur, the valve may malfunction and exhibit minor symptoms, such as irregular flow performance, or behavior indicative of more serious damage, such as accidental drug overdelivery due to sudden opening of the valve, no delivery of the drug due to obstruction of the valve, or leakage of the pump due to over-pressure for the drug reservoir. These negative effects are generally enhanced with smaller structures and lumina.

Accordingly, there is a need for reliably performing micro-scale check valves and methods for their reproducible manufacture.

SUMMARY

Embodiments of the present invention provide various check-valve structures, typically consisting of only few components, that are amenable to manufacture at microscales (i.e., with dimensions of 1 mm or less) while achieving adequate performance characteristics for use in small drug pumps or other medical microdevices. In general, these valve structures are passive in-line diaphragm valves, including, in the simplest embodiment, a rigid tube segment (e.g., less than 1 mm in diameter and/or length) for fluid flow therethrough, and a slitted elastomeric diaphragm spanning the cross-section of the tube segment; the diaphragm may extend into a skirt by which it can be secured to the interior surface of the tube. Application of a sufficient forward pressure (i.e., pressure driving fluid in the desired flow direction) onto the diaphragm causes the slit to "crack" open and permit fluid to pass; under pressure in the reverse direction, however, the slit remains closed until a breakdown pressure significantly higher than the cracking pressure is reached. (A "slit," as used herein, denotes a normally closed passage that can be opened to allow fluid flow therethrough by application of pressure, as created, e.g., by creating a cut through the diaphragm with a piercing tool that removes no or only minimal material (such that the width of the slit, in the closed state, is close to zero.) The simplicity of this valve structure contributes to its manufacturability at microscales. In addition, the straight fluid path through the valve, and the absence of substantial corners and dead spaces, reduces the risk of valve clogging, and thereby lengthens the lifetime of the valve.

Various embodiments utilize additional valve components to further increase valve performance. For example, the breakdown pressure can be increased by forming a bump on the downstream (fluid-exit) side of the diaphragm (i.e., the side onto which any backpressure acts) in the location of the slit. In certain embodiments, the valve further includes a backward-leakage stopper placed against the upstream (fluid-entry) side of the diaphragm and fitted into or around the inlet end of the tube, which inhibits backward bending of the diaphragm under backpressure and, thus, prevents leakage. In some embodiments, the valve includes a push-rod or other suitable member that "pre-loads" the diaphragm by bending it in the forward direction; such pre-loading may serve to reliably engineer a specific valve cracking pressure. The pre-load member is placed so as to cover the slit or, in alternative embodiments, a permanent opening in the diaphragm.

Accordingly, in one aspect, the invention pertains to an in-line check valve including a tube defining a lumen for flow of fluid therethrough, and an elastic diaphragm affixed to an interior surface of the tube and spanning a cross-section thereof. The diaphragm may extend into a skirt secured to the interior of the rigid tube; the tube may have holes through a side wall thereof in regions adjacent the skirt, which may be secured to the rigid tube by a bonding material such as epoxy extending through the holes. The elastic diaphragm includes a slit or an opening therethrough, and is configured to open upon application of at least a cracking pressure on a first side of the diaphragm so as to permit fluid to pass through the slit or opening from the first side to a second side of the diaphragm, and to prevent backflow of fluid from the second side to the first side until at least a breakdown pressure is reached on the second side. In various embodiments, the tube diameter, and/or the largest dimension of the valve, is less than 1 mm. In various embodiments, the check valve further includes a pre-load member urged against the first side of the diaphragm so as to flex the diaphragm and occlude the slit or opening in a closed state of the valve; the cracking pressure depends at least in part on an axial position of the pre-load member.

The diaphragm may include a slit therethrough that is configured to flex and open upon application of at least the cracking pressure on the first side of the diaphragm. In some embodiments, the slit is co-located with (i.e., extends through) a bump on the second side of the diaphragm. In some embodiments, the valve includes a backward-leakage stopper abutting the diaphragm at the first side thereof. The stopper may include a stopper tube fitted to an interior of the valve tube; the stopper tube may have a lumen, or multiple lumina, therethrough, which may be sized to impose a specified restriction on the rate of fluid flow therethrough. In the case of a single lumen, the lumen may be centered at the slit, or offset therefrom. In some embodiments, the stopper extends beyond and surrounds an inlet end of the rigid tube.

In another aspect, the invention is directed to a method for fabricating an in-line valve structure using a stack mold fixture. In various embodiments, the stack mold fixture includes one or more pins having a first tier with a first diameter and a second tier with a second diameter that is smaller than the first diameter, and one or more spacers that extend in height beyond the pin. The first, larger-diameter tier may include one or more exit flow channels. The method includes placing a valve tube having an inner diameter matching the first diameter over the pin, e.g., on top of an O-ring resting on the support surface from which the first tier of the pin extends. Further, the method involves filling liquid elastomer precursor into an interior space of the valve tube (before or after tube placement over the pin). Liquid elastomer precursor may then be forced from the interior space of the valve tube, e.g., through the exit flow channel(s), thereby forcing a surface of the liquid elastomer to a height of the spacer(s). In some embodiments, the liquid elastomer is forced from the tube interior by placing a flat member on the spacer(s). The flat member may be coated, prior to placement on the spacer, with an adhesion-inhibiting coating, such as parylene or gold. The stack mold fixture may include first and second bracket members, and the pin(s) and the flat member may be secured therebetween.

The method further includes curing the elastomer precursor, and thereby creating in the valve tube a diaphragm having a thickness equal to the distance by which the at least one spacer extends in height beyond the pin. In some embodiments, a recess is etched into the flat member prior to placement on the spacer; curing, thus, causes creation, in the diaphragm, of a bump complementary to the recess. The curing process may also cause creation of a skirt extending from the diaphragm and having a distance equal to half a difference between the first and second diameters; the length of the skirt may be equal to a height of the second tier or adjusted by alternating the fill volume of liquid elastomer precursor. In some embodiments, liquid elastomer forced from the interior space of the valve tube is removed prior to curing. Following curing, the valve tube and diaphragm may be removed from the stack mold, and a slit or opening may be created in the valve diaphragm. In various embodiments, the stack mold fixture comprises multiple pins; in this case, the method may involve creating multiple valve structures simultaneously.

Still another aspect of the invention relates to an in-line check valve in which a first tube defines a first lumen for flow of fluid therethrough; affixed to the interior surface of the first tube and spanning a cross-section thereof, an elastic diaphragm having a slit or opening therethrough; and a backward-leakage stopper that extends beyond (i.e., upstream of) and surrounds an inlet end of the first tube, is affixed to the exterior surface of the first tube, and abuts the diaphragm at the first side thereof. In some embodiments, the valve is configured to (i) open upon application of at least a cracking pressure on the first side of the diaphragm so as to permit fluid to pass through the slit or opening from the first side to the second side of the diaphragm, and (ii) prevent backflow of fluid from the second side to the first side until at least a breakdown pressure is reached on the second side. The diameter of the first tube may be less than 1 mm. In one implementation, the largest dimension of the valve is less than 1 mm.

In various embodiments, the elastic diaphragm extends into a skirt secured to the interior surface of the first tube. The first tube may include holes through a side wall thereof in regions adjacent the skirt. The skirt is then secured to the first tube by epoxy extending through the holes. In addition, the diaphragm may include a bump on the first side; the slit is co-located with the bump. In some embodiments, the slit or opening is configured to flex and open upon application of pressure at least equal to the cracking pressure on the first side of the diaphragm.

In one embodiment, the stopper includes the second lumen therethrough. The second lumen may be sized to impose a specified restriction on a rate of fluid flow therethrough. In addition, the second lumen may be centered at the slit or opening. Alternatively, the stopper may have multiple lumina therethrough. In some embodiments, the stopper further includes a pre-load member urged against the first side of the diaphragm so as to flex the diaphragm and occlude the slit or opening in a closed state of the valve. The cracking pressure may depend at least in part on an axial position of the pre-load member.

BRIEF DESCRIPTION OF THE DRAWINGS

The foregoing will be more readily understood from the following detailed description of the invention, in particular, when taken conjunction with the drawings, in which:

FIGS. 3A-3E illustrate the operation of the valve structure of FIGS. 2A and 2B;

FIGS. 5A-5D illustrate the operation of the valve structure of FIGS. 4A and 4B;

FIGS. 7A-7D illustrate the operation of the valve structure of FIG. 6A;

FIGS. 8A-8D illustrate the operation of the valve structure of FIG. 6B;

FIGS. 16A-16I illustrate a method for creating the valve of FIGS. 2A and 2B by micromachining and molding in accordance with various embodiments;

FIGS. 20A-20C, 21A-21G, and 22A-22G illustrate methods for creating the valve of FIG. 6A by affixing a backward-leakage stopper to the interior of the valve tube in accordance with various embodiments;

FIGS. 23A-23F illustrate methods for creating the valves of FIGS. 10A and 10B by affixing a push-rod to the interior of the valve tube in accordance with various embodiments;

DETAILED DESCRIPTION

1. Valve Performance Characteristics

Figure 1:
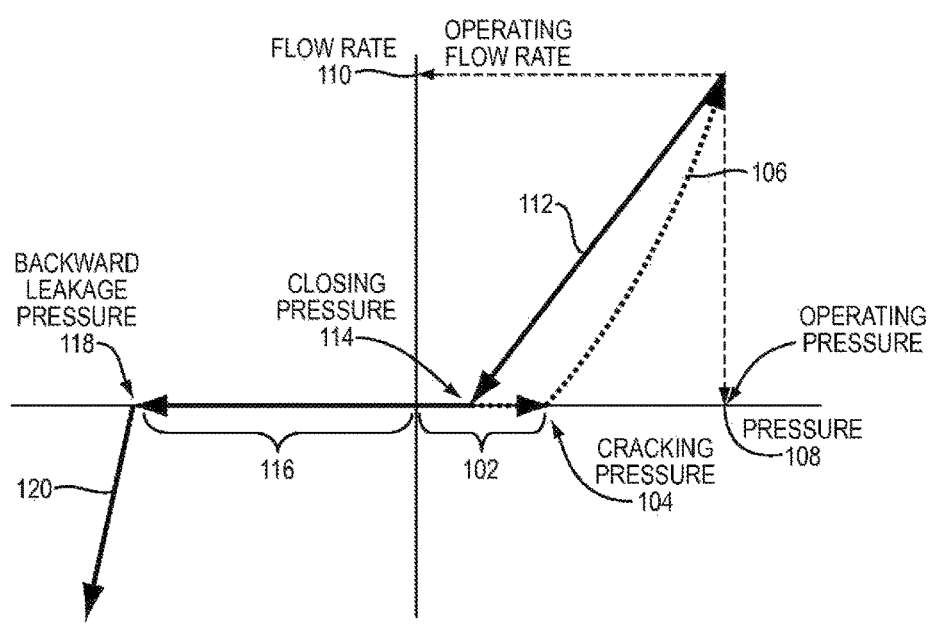
FIG. 1 is a flow/pressure curve illustrating performance parameters of an ideal check valve.

The present invention relates to one-way check valves that achieve, in various embodiments, superior performance characteristics. Parameters that are commonly used to define the performance of check valves are illustrated in FIG. 1, which depicts an ideal flow/pressure curve for a normally-closed one-way check valve. When pumping begins and pressure increases from zero to positive pressures (i.e., pressures with a negative gradient in the desired flow direction), the valve remains closed, i.e., the flow rate remains zero (curve segment 102), until the cracking pressure 104 is reached. Once the cracking pressure 104 has been passed, the flow rate increases with increasing pressure (curve segment 106). However, in pump systems that employ a feedback loop, a steady-state operating pressure 108 and corresponding operating flow rate 110 are actively maintained once attained. When the pump is turned off (which generally happens after the targeted delivery volume has been dispensed), the pressure and flow rate decrease (curve segment 112). The flow rate typically drops to zero at a pressure 114 less than or equal to the cracking pressure 104; this pressure is generally called closing pressure or shut-off pressure. A non-zero difference between cracking pressure and closing pressure results from stiction (i.e., van der Waals forces) between the material surfaces interfacing at the valve slit. In some situations, the valve is subjected to backpressure or a vacuum (i.e., underpressure) inside the pump, i.e., the pressure reverses and becomes negative. If this occurs, fluid flow is prevented or "checked" (curve segment 116) until a breakdown pressure 118 (or backward-leakage pressure) is reached. At the breakdown pressure 118, the integrity of the valve structure is ruined, either temporarily or permanently, permitting fluid to flow in the backward direction (curve segment 120).

Pump-device control generally takes the pressure/flow characteristics of the pump into account. Accordingly, predictable pump operation is contingent on reliable knowledge of the pressure/flow curve and, in particular, the cracking pressure, shut-off pressure, and breakdown pressure of the pump. Reliability, however, is a major challenge for microscale valves. When multi-component state-of-the-art check-valve structures produced with the same technology as is used for macroscale valves are scaled down to dimensions of less than 2 mm (as required for small-footprint pump devices), their flow/pressure behavior tends to become unrepeatable and unreliable. In addition, complicated check-valve structures shorten the lifetime of the devices, and can cause serious failure when used in long-term implants. For example, complex fluid paths with dead spaces and corners render many conventional valve structures susceptible to clogging. To address these challenges, the present invention provides various simpler valve structures with reproducible flow/pressure behavior.

Another challenge in designing valve structures arises from factors that affect pump operating conditions, especially fluctuations of the external pressure (i.e., the atmospheric pressure or environmental pressure), which may change according to the patient's environment. External pressure fluctuations can cause a drug-pump device to either overdose or underdose. In extreme cases, a sudden external pressure drop can induce an accidental delivery of the drug even when the power to the pump is completely shut off because the valve is forced open when the pressure difference reaches the cracking pressure. Two common examples of situations in which patients can experience external pressure drops in their normal daily lives are highway driving in mountainous areas and taking off in an aircraft. During aircraft take-off, for example, the pressure can drop 3.8 psi or more. Therefore, to avoid malfunction (especially in devices where pressure does not equilibrate with the outside pressure, such as drug pump devices with rigid reservoir enclosures), implanted valves are preferably able to withstand pressure drops of at least 3.8 psi, i.e., have cracking pressures of at least that value. In various embodiments, the present invention allows this requirement to be met by providing valve structures with features that increase the valve cracking pressure, such as a push-rod for pre-loading the valve diaphragm.

In addition to accidental opening of the valve due to external pressure decreases, delayed closing of the valve when the pump is shut off can cause overdosing. A major risk interval is the time period close to the end of a scheduled dose delivery, when the combined effect of air-bubble formation and expansion in the drug reservoir and an external pressure drop can cause drug to be pushed out of the device before the valve can completely shut off flow, risking serious overdosing. Therefore, shut-off pressures, like cracking pressures, are desirably higher than the external pressure drop (and, thus, close to the cracking pressure). In regular macro-scale check valve designs, a high and reliable shut-off pressure can be achieved simply by using a valve-seat-restoring mechanism to provide a pre-loading force that shuts off fluid flow (i.e., reaches either zero flow or a pre-defined, minimum flow rate that is negligible for practical purposes in the intended application context) long before the valve driving pressure goes down to zero. Usually, the restoring force is provided by a spring (e.g., a coil spring, spiral spring, tether spring, or disk spring). Once again, however, these spring mechanisms are difficult to miniaturize down to sub-millimeter scale, and are challenging to integrate into the housing of a microscale check valve. In the present invention, a restoring mechanism is provided by the elastic diaphragm, which, in various embodiments, rests against a push-rod or stopper structure acting as a valve seat.

2. Valve Structures and Operation

Figure 2A:
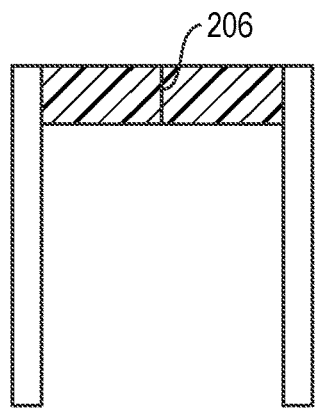
FIGS. 2A and 2B are side and perspective views, respectively, of a basic valve structure in accordance with one embodiment.
Figure 2B:
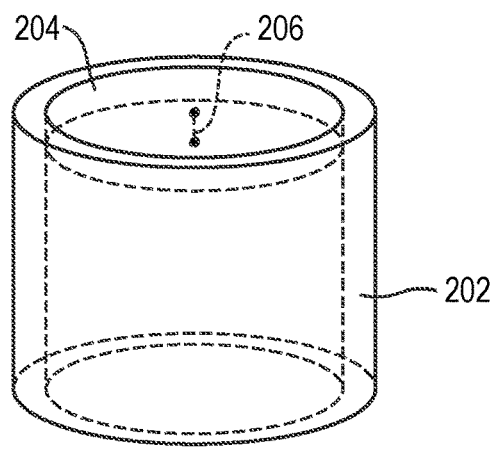
Figure 2C:
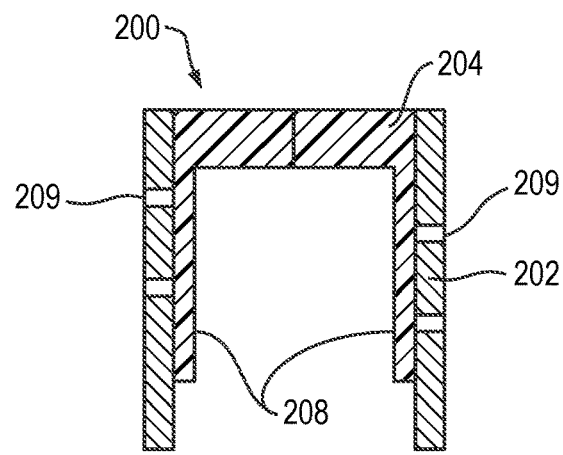
FIG. 2C is a side view of a basic valve structure including a diaphragm skirt in accordance with various embodiments.

FIGS. 2A and 2B illustrate a simple check-valve structure in accordance with one embodiment. Due to its minimalistic design, i.e., the small number of components, this structure is amenable to microscale implementation while offering accurate, repeatable, and reliable flow/pressure performance. As shown, the valve 200 includes a rigid valve tube 202 and an elastomer diaphragm 204 spanning a cross-section of the tube 202. The diaphragm 204 includes, in a central region, a slit 206 that is normally closed due to stiction forces, but opens up when the diaphragm is bent upon application of pressure. The diaphragm typically has a thickness, relative to the tube diameter, between about 1% and about 100%, and may be made, e.g., of silicone rubber (such as LSR, HCE, LCE, etc.), synthetic rubber (such as EPDM, Butyl, Buna, etc.), natural rubber, thermoplastic elastomers, or generally any viscoelastic polymer material with adequate performance and durability characteristics. Its durometer, i.e., hardness, can be adjusted during diaphragm manufacture by means of the material composition, baking parameters, etc. The tube may be made of a hard polymer (such as, e.g., PEEK, polycarbonate, or acrylic), glass, metal, ceramics, silicon, oxides, composite materials, or generally any rigid materials. Its dimensions (e.g., diameter and/or length) are preferably smaller than 1 or 2 mm.

The cross-section of the valve tube 202 and the diaphragm 204 may be circular as shown, or have any of a variety of different shapes. For example, they may form squares, triangles, pentagons, hexagons, other polygons (whether regular or irregular), ellipses, etc. Moreover, the outer cross-section of the tube (defined by its exterior wall(s)) may differ from the inner cross-section (defined by the interior wall(s)) and diaphragm (whereas the inner cross-section and diaphragm typically match to allow the diaphragm to be properly sealed against the inner wall of the tube). For example, the tube may have a square-shaped or rectangular outer cross-section that facilitates convenient assembly into the pump, and a circular inner cross-section that promotes uniform, laminar fluid flow and avoids vortices at which drug might otherwise sedate. The elastomer diaphragm 204 may be attached to the inner surface of the rigid valve tube 202 at or near the outlet end (as shown), at or near the inlet end of the tube 202, or in the middle region of the tube, i.e., displaced from the ends of the tube 202.

The elastomer diaphragm 204 may be bonded to the interior of the valve tube 202 with a suitable adhesive, such as silicone adhesive, epoxy, acrylic adhesive, etc. The choice of adhesive depends generally on the material of the diaphragm 206. For instance, an adhesion promoter may be used for a silicone-rubber diaphragm, epoxy is suitable for a thermal-plastic or synthetic-rubber diaphragm, and acrylic adhesive may be preferable for a PMMP diaphragm. Alternatively, adhesion of the diaphragm may be effected by curing an elastomer precursor in place to form the diaphragm; in this case, the diaphragm 204 is either bonded directly to the valve tube 202, or via a layer of adhesion promoter coated onto the interior surface of the valve tube 202. In general, any kind of bonding technique may be employed; suitable techniques include, e.g., thermal bonding, ultrasonic bonding, infrared (IR) bonding, plasma bonding, etc. In some embodiments, the bonding surface is defined by the circumference and thickness of the diaphragm (as shown); in other embodiments, the bonding surface is enlarged by means of a tubular "skirt" 208 that is formed integrally with and extends from the circumference of the diaphragm 204. Such a skirt 208 has the added benefit of further inhibiting leakage as it increases the area of contact between the valve tube 202 and the diaphragm 204 through which any leaking fluid would necessarily pass. In one embodiment, the rigid tube 202 has holes 209 through wall sections adjacent the skirt 208, which allow epoxy or another glue to flow therethrough to create an interlocking interface between the valve tube 202 and the skirt 208. Various valve structures described below are depicted without a skirt for greater clarity; it should be understood, however, that these structures can straightforwardly be modified to include a skirt extending from the diaphragm.

FIGS. 3A-3E conceptually illustrate the operation of the check valve 200, which may, as shown, be inserted into outer tubing (of which only a portion is shown for ease of illustration). If pressure is applied on the upstream side 300 of the diaphragm (i.e., in the forward flow direction), the rigid valve tube provides a fixed boundary for the elastomer diaphragm so that the diaphragm bends and the internal stress inside the diaphragm increases (FIG. 3A). When the cracking pressure Pa, of the valve is reached, the internal stresses begin to exceed the maximum stiction force around the slit, and the valve "cracks open" (FIG. 3B), permitting the pressurized fluid (e.g., a drug solution) to pass through the valve opening to the downstream region. The gap width of the opened slit provides a flow resistance to the fluid that is approximately proportional to the degree of diaphragm bending. In principle, the higher the driving pressure, the more the diaphragm will deflect, and the wider the gap will become. Consequently, the higher the driving pressure, the higher the drug flow rate will generally be.

When the pressure drops, the flow rate decreases until the valve opening closes back up (FIG. 3C). The occurrence of this closing action at positive pressure Pa results from diaphragm bending under fixed-boundary conditions at low stress levels, a phenomenon well-known to those familiar with the fundamentals of plate-and-shell mechanics. If pressure is applied in the backward direction (i.e., backpressure on the downstream side 302 of the diaphragm 204 or if vacuum pressure develops upstream, e.g., in the drug reservoir as drug is pumped out), the diaphragm 204 bends backwards (FIG. 3D). The slit 206 first stays closed, preventing fluid flow in the backward direction. If the pressure continues increasing, however, the valve breaks down when the backward pressure reaches the breakdown pressure Pbd (which will generally be different from the cracking pressure if additional structural features that break the symmetry of the configuration, such as the bump or backward-leakage stopper discussed below, are included in the valve) (FIG. 3E).

Figure 4A:
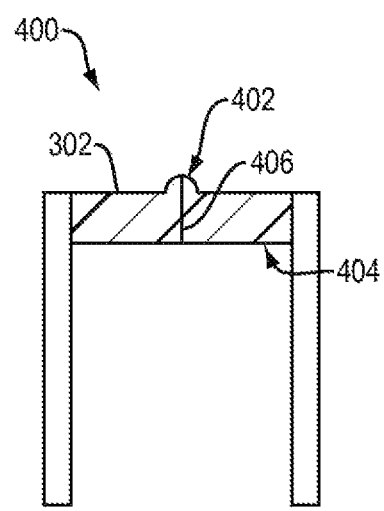
FIGS. 4A and 4B are side and perspective views, respectively, of a valve structure with a sealing bump in the diaphragm in accordance with one embodiment.
Figure 4B:
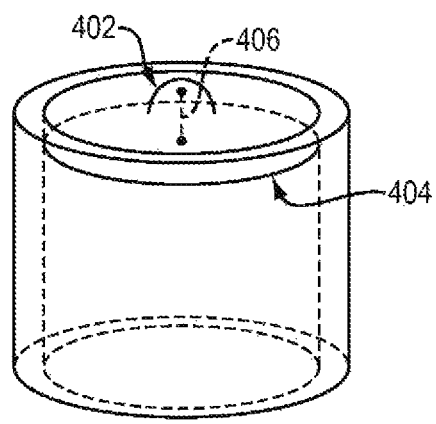

FIGS. 4A and 4B illustrate a modified check valve 400, which can withstand higher backpressures from the downstream region than the check valve 200 of FIGS. 2A and 2B due to a "sealing bump" or protrusion 402 formed on the downstream side of the diaphragm 404. In this embodiment, the slit 406 is created within (i.e., co-located with) the bump 402, causing the bump 402 to increase the sealing force of the slit interface under backpressure, thereby increasing the breakdown pressure. (Apart from the sealing bump 402, this valve 400 shares a similar structure with the previously described valve 200.) FIGS. 5A-5D illustrate the operation of the valve 400. In particular, FIGS. 5C and 5D show how backpressure exerted on the diaphragm tends to compress the bump 402, thereby increasing the sealing forces at the slit interface, resulting in significantly higher breakdown-pressure performance. While depicted as a hemisphere, the bump 402 may also be shaped like a hemi-ellipsoid, hemi-paraboloid, square block, pyramid, prism, cone, etc. Importantly, the bump should be overall convex to effect the desired increased sealing forces; the particular shape is not crucial.

Figure 6A:
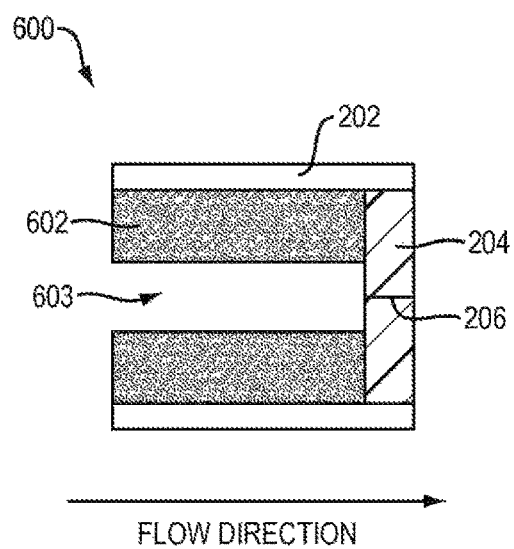
FIGS. 6A and 6B are side views of valve structures with backward-leakage stoppers in accordance with various embodiments.
Figure 6B:
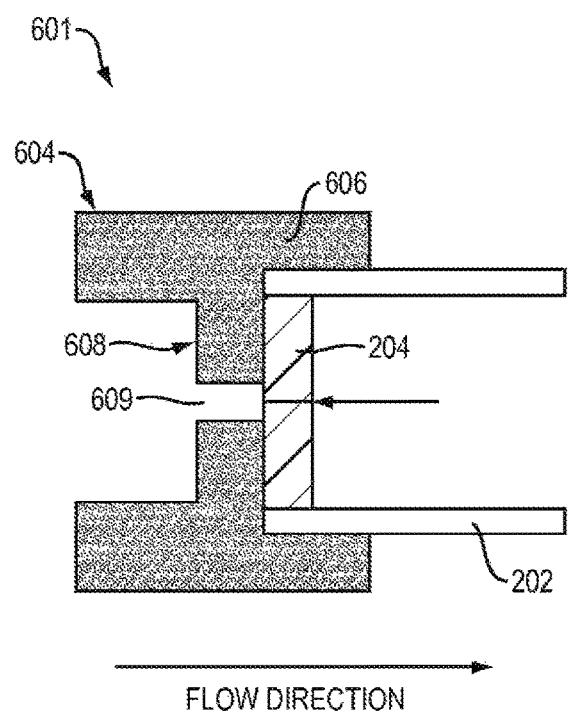

FIGS. 6A and 6B show valve embodiments 600, 601 that include, in addition to the rigid tube 202 and diaphragm 204, a structure 602 or 604 adjacent the upstream side of diaphragm 204 that inhibits backward bending of the diaphragm 204 and thereby increases the breakdown pressure and/or otherwise eliminates or reduces backward leakage (including, e.g., leakage of fluid permeating the diaphragm material itself). In FIG. 6A, the "anti-bending structure" or "backward-leakage stopper" 602 includes or consists of a tube with an outer diameter fitted to the inner diameter of the main valve tube 202, and an inner diameter defining a bore 603 that is aligned with the diaphragm slit 206. Alternatively, the anti-bending structure may extend to the exterior of the valve tube 202. For instance, in FIG. 6B, the anti-bending structure 604 is integrated with tubing 606 upstream of the valve, and includes a wall 608 spanning the cross-section of the outer tubing 606 and located immediately adjacent to the diaphragm 204, which is, in this embodiment, placed at the inlet end of the valve tube 202. A central opening or bore 609 through the wall 608 of the anti-bending structure 604 is aligned with the slit 206 in the diaphragm 204 to allow the valve 601 to open and permit fluid to pass through. The anti-bending structures 602, 604 may be made of polymers, glass, metal, ceramics, silicon, oxides, composite materials, or other materials, and may be more or less rigid than the valve tube 202.

Both backward-leakage stoppers 602, 604 provide a supporting structure that resists backward bending of the check-valve diaphragm 204, thereby increasing backward-leakage pressure. More specifically, with reference to the structure 602 of FIG. 6A, the stopper tube is in contact with the upstream surface of the diaphragm (albeit with zero or nearly zero contacting force). When backpressure is exerted on the diaphragm 204, diaphragm bending is restricted to the area within the inner diameter of the stopper tube, whereas bending of the outer ring of the diaphragm is resisted by the stopper. Diaphragm deformation is, thus, considerably limited, and as a result, significantly higher backpressures are required to break down the diaphragm, offering better backward-leakage performance. This working principle of the backward leakage stopper 602 is illustrated in FIGS. 7A-7D. As will be readily apparent, the anti-bending structure 604 integrated into the upstream tubing 606 functions similarly, as it restricts diaphragm bending to the region adjacent the opening 609 in the stopper wall 608, as shown in FIGS. 8A-8D. In addition to blocking backward fluid leakage, the stoppers also function as flow restrictors in the forward direction; their inner diameters may be tailored to a specified flow rate.

Figure 8E:
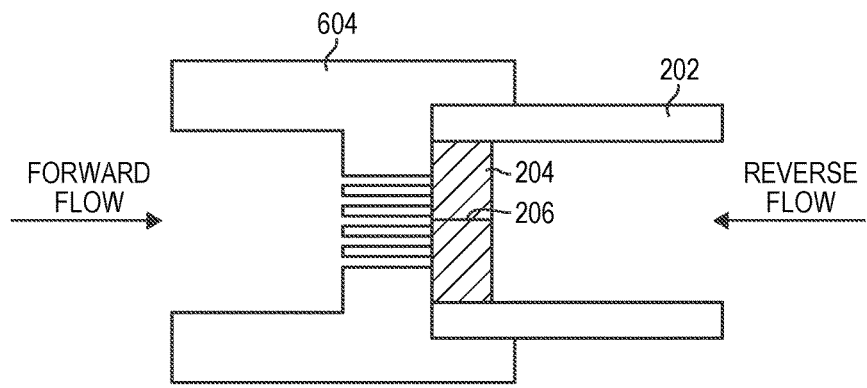
FIG. 8E illustrates a backward-leakage stopper with multiple bores in accordance with one embodiment.

Referring to FIG. 8E, the anti-bending structure 604 may include multiple bores or lumina for fluid flow therethrough. In one embodiment, at least one of the bores or lumina is aligned with the slit 206 in the diaphragm 204. Alternatively, none of the bores or lumina is aligned with the slit 206. Implementations with multiple lumina may allow valve functionality to be maintained if one or more (but fewer than all) of the lumina become clogged. In addition, the lumen size may be adjusted to modify the cracking pressure. The total lumen cross section determines the flow resistance imposed by the anti-bending structure 604; thus, the anti-bending structure 604 functions additionally as a flow restrictor.

Figure 8F:
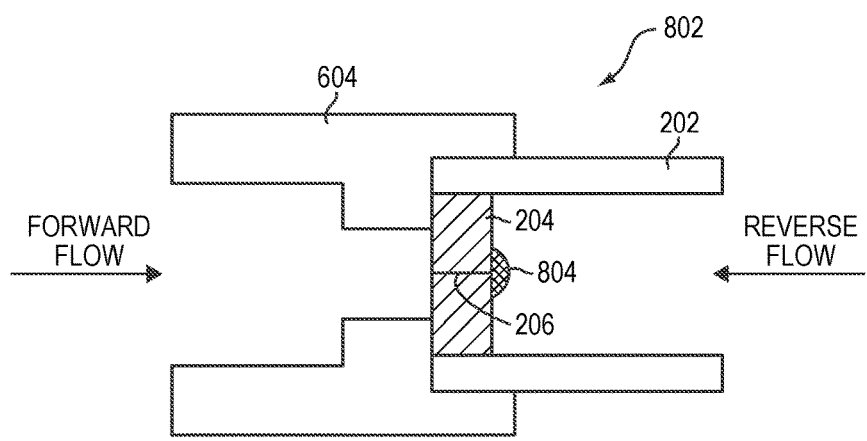
FIG. 8F illustrates a valve structure with a backward-leakage stopper and a sealing bump in the diaphragm in accordance with one embodiment.

FIG. 8F illustrates a modified check valve 802, which can withstand higher backpressures from the downstream region than the check valve 601 of FIG. 6B and FIGS. 8A-8D due to a "sealing bump" or protrusion 804 formed on the downstream side of the diaphragm 204. (Apart from the sealing bump 804, this valve 802 shares a similar structure with the previously described valve 601.) In this embodiment, the slit 206 is created within (i.e., co-located with) the bump 804, causing the bump 804 to increase the sealing force of the slit interface under backpressure, thereby increasing the breakdown pressure. This is because backpressure exerted on the diaphragm tends to compress the bump 804, thereby increasing the sealing forces at the slit interface and resulting in significantly higher breakdown-pressure performance. While depicted as a hemisphere, the bump 804 may also be shaped like a hemi-ellipsoid, hemi-paraboloid, square block, pyramid, prism, cone, etc. Importantly, the bump 804 should have an overall convex contour to effect the desired increased sealing forces; the particular shape is not crucial.

Figure 8G:
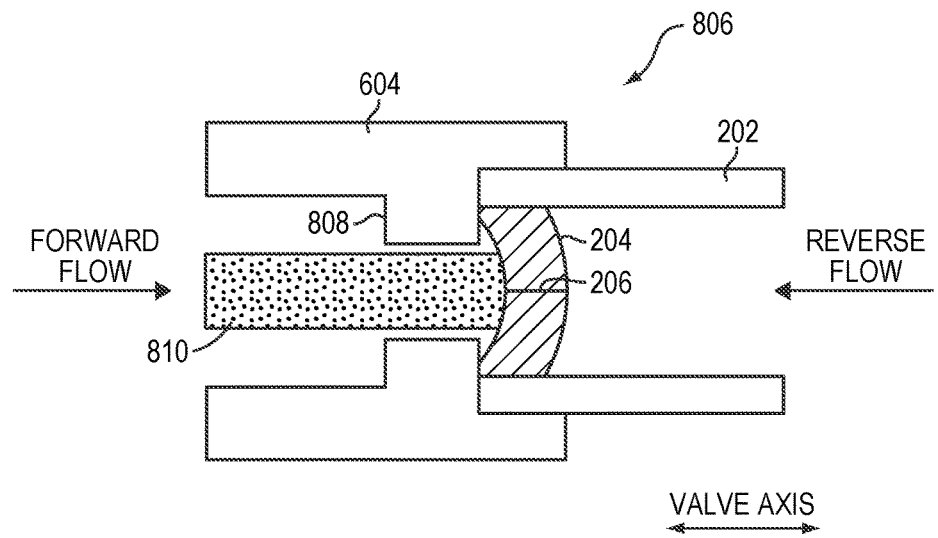
FIGS. 8G and 8H illustrate a valve structure with a backward-leakage stopper and a push-rod in the diaphragm in accordance with one embodiment.

FIG. 8G illustrates another check valve 804, which is based on the check valve 601 of FIG. 6B and FIGS. 8A-8D but has been modified to increase the cracking pressure and to withstand higher backpressures from the downstream region. The check valve 804 includes a push-rod 810 pressing against the valve diaphragm 204, forcing the diaphragm to deform; the extent of deformation is dependent upon the position of the push-rod 810 along the valve axis, and can, thus, be controlled (during manufacture) by moving the push-rod 810 to the desired axial position. The preloading force creates a seal between the diaphragm 204 and the push-rod 810. Thus, to open the valve 806, the pump pressure needs to break this seal, i.e., overcome the preloading force from the push-rod 806 in addition to the stiction of the diaphragm slit 206. Consequently, the push-rod 810 increases the cracking pressure, compared with that of, e.g., the valve 601 shown in FIG. 6B and FIGS. 8A-8D, which has a planar slitted diaphragm.

Once forward pressure reaches the pre-loading force of the push-rod 810, the valve 806 opens and allows liquid to flow around the push-rod 810 through the valve slit 206. However, when backpressure is applied, the push-rod 810 plays a role similar to that of the backward-leakage stopper discussed above and prevents back flow by sealing of the diaphragm 204 against the push-rod surface. In some embodiments, the push-rod 810 preferably has a very smooth front surface shaped with constant or continuously and slowly varying curvature so as to ensure a good seal between the valve diaphragm 204 and the push-rod 810. The front surface of the push-rod 810 may be shaped, e.g., like a hemisphere, hemi-ellipsoid, or hemi-paraboloid, etc. Acceptable degrees of surface roughness and/or bumpiness of the push-rod are generally a function of tolerable leakage levels. For a leakage limit of 0.5 nl/min, for instance, the roughness generally ought to be below 16 microinches.

Figure 8H:
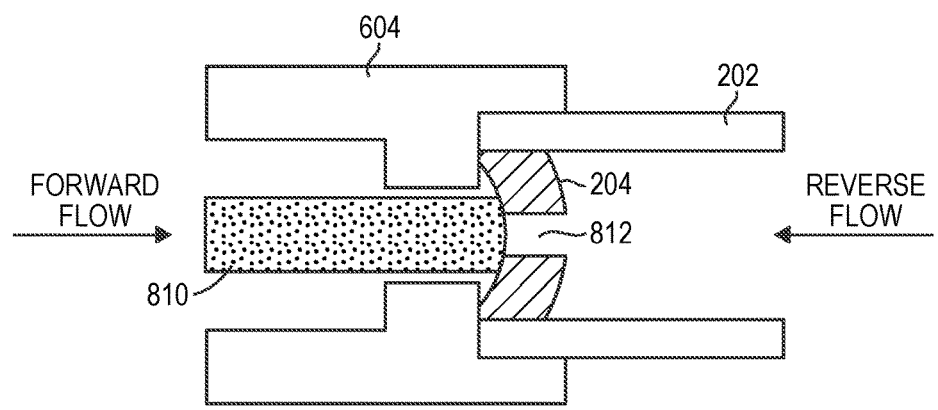

Referring to FIG. 8H, in various embodiments, the valve 604 has, instead of a slit, a permanent opening 812 in the diaphragm 204 such that only the pre-loading force from the push-rod 810 holds the valve sealed before forward pressure is applied. Stiction forces are eliminated (or at least reduced) from this valve, and once the forward pressure reaches the pre-loading force of the push-rod 810, the valve opens and allows liquid to flow therethrough. Since stiction forces are generally less reliable than pre-loading forces, this valve structure is advantageous when very accurate cracking pressures are desired.

Figure 9A:
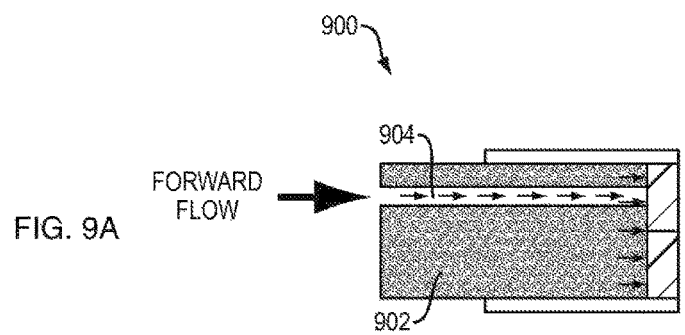
FIGS. 9A-9D illustrate the operation of a valve structure with a backward-leakage stopper having an off-axis bore in accordance with one embodiment.
Figure 9B:
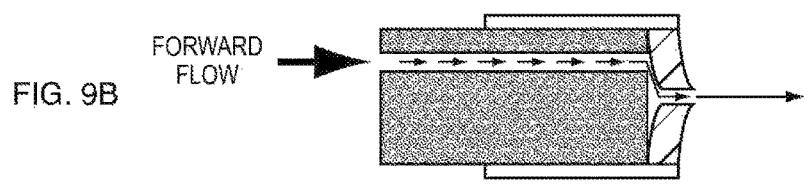
Figure 9C:
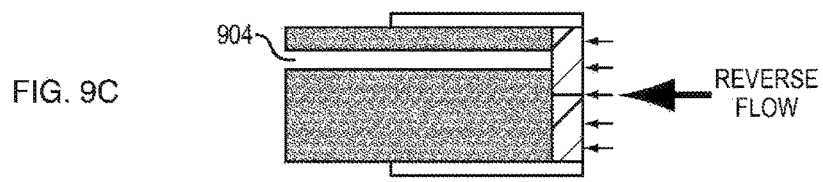
Figure 9D:
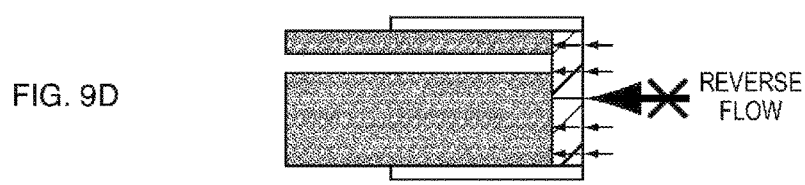
Figure 9E:
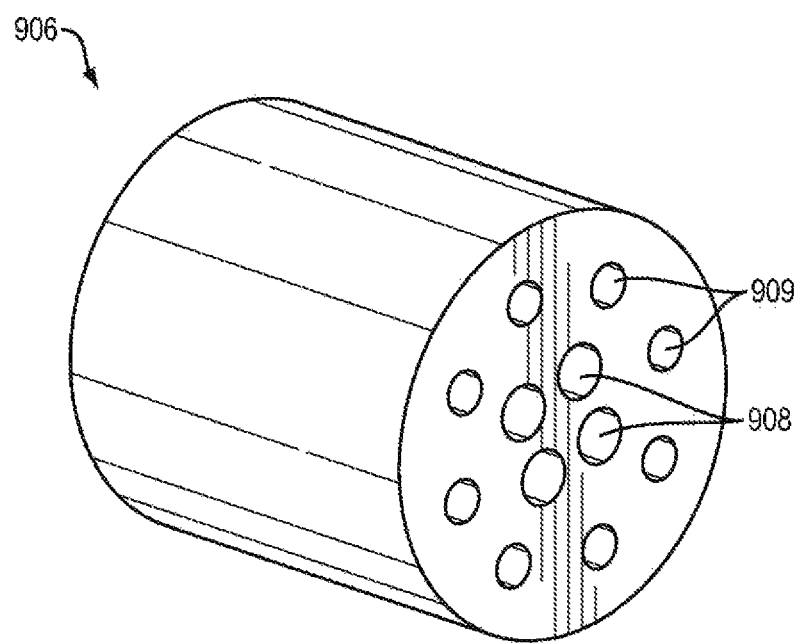
FIGS. 9E and 9F illustrate, in perspective and side views, respectively, a backward-leakage stopper with multiple symmetrically arranged bores in accordance with one embodiment.
Figure 9F:
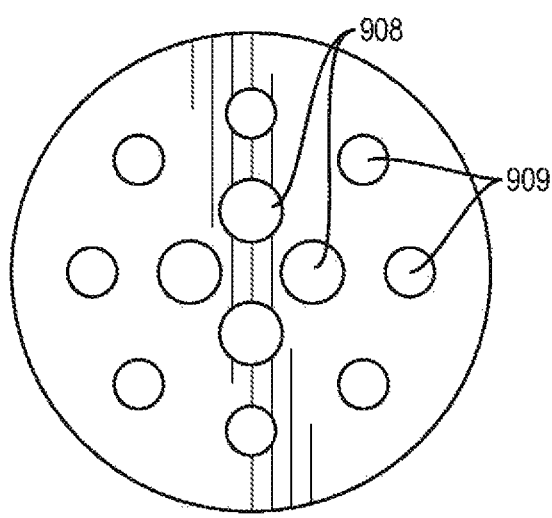

The shape and location of the bore or opening 603, 609 in the stopper 602, 604 may be varied. In the embodiments shown in FIGS. 6A and 6B, the opening is circular and centered within the valve tube 202. In alternative embodiments, the bore or opening is shaped, e.g., like a square, ellipse, triangle, etc. Further, the opening 603, 609 may be located off-center, and need not even overlap with the diaphragm slit 206. FIGS. 9A-9D, for example, show a valve 900 including a tubular anti-bending structure 902 with an off-center bore 904. In this embodiment, opening the valve requires the diaphragm 204 to bend sufficiently, due to pressure exerted by fluid flowing through the bore, to create a fluidic path extending from the bore, between the front surface of the stopper and the diaphragm, to the opened slit 206. Backward-leakage stoppers may also be provided with multiple bores or through-holes, optionally having different geometries. Further, the bores need not be straight and parallel to the valve axis, but may be curved, zigzagged, or wavy, for example. In other embodiments, the bores are formed by one or more grooves machined into an otherwise solid anti-bending rod. The number and shape of the grooves can be varied. Such an anti-bend rod can also be machined half-way with multiple channels connected to a stepped-down outer diameter on the other end. Of course, bores and/or grooves of different shapes and sizes can also be combined in various ways, as will be readily apparent to one of skill in the art. The particular design and arrangement may be adjusted to achieve a particular desired combination of cracking pressure, operational flow rate, and backward-leakage pressure. Multiple bores or grooves may serve to provide redundant flow paths in case of a blockage of one or more of the paths. In one embodiment of a stopper 906, shown in FIGS. 9E and 9F, multiple bores of different sizes are arranged along two concentric circles, with larger-diameter bores 908 placed around the inner and smaller-diameter bores 909 placed around the outer circle. Many other patterns of bores are, of course, possible; preferably, the pattern is symmetrical so as to avoid biasing some portions of the diaphragm to flex significantly more than others. Furthermore, the bore(s) preferably do not overlap with the diaphragm opening (or slit) such that the opening is adjacent a solid portion of the stopper, preventing any backwards leakage as long as the integrity of the stopper is maintained.

Figure 10A:
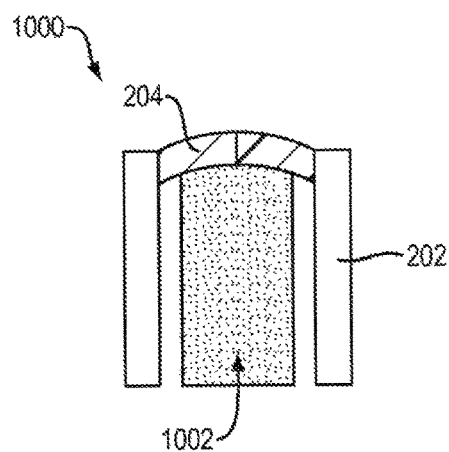
FIGS. 10A and 10B are side and isometric views, respectively, of a valve structure with a push-rod for pre-bending the valve diaphragm in accordance with various embodiments.
Figure 10B:
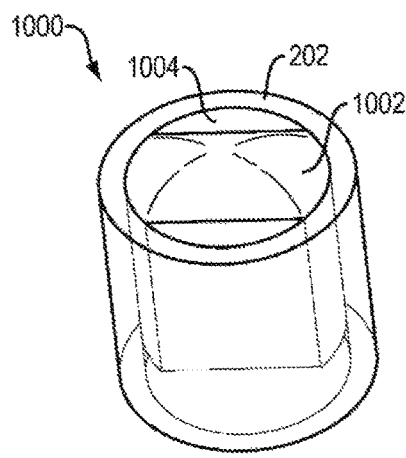

In various embodiments, illustrated in FIGS. 10A and 10B, the valve 1000 includes a push-rod 1002 which "pre-bends" or "pre-loads" the valve diaphragm 204 to provide higher forward cracking pressure. The push-rod 1002, which may be made, e.g., of a polymer, glass, metal, ceramics, silicon, oxides, composite material, or other materials, is generally placed inside the valve tube 202 along the axis of the tube 202. As can be seen in FIG. 10B, the push-rod 1002 may, in one cross-sectional dimension, match the inner diameter of the valve tube 202 so that it can be bonded thereto. In another (e.g., perpendicular) cross-sectional dimension, the width of the push-rod 1002 may be smaller than the inner diameter of the tube 202 so that a space 1004 through which fluid can flow remains. Alternatively, the push-rod may have a circular cross-section with a diameter equal to the inner diameter of the valve tube 202, and include one or more bores or lumina for fluid flow therethrough, allowing the rod diameter to match the inner diameter of the valve tube. Bore arrangements may be similar to those discussed above for the backward-leakage stopper (e.g., in FIGS. 9E and 9F). Implementations with multiple lumina allow valve functionality to be maintained if one or more of the lumina (but fewer than all) become clogged. The lumen size and distance from the diaphragm slit or opening may be adjusted to modify the cracking pressure. The total lumen cross section determines the flow resistance imposed by the push-rod; thus, the push rod functions additionally as a flow restrictor. In yet another embodiment, the push-rod may have a circular cross-section with a diameter smaller than the inner tube diameter, and may be suspended inside the valve tube with struts or similar structural features.

During valve manufacture, the push-rod 1002 is pressed against the valve diaphragm 204, forcing the diaphragm to deform; the extent of deformation is dependent upon the position of the push-rod 1002 along the valve axis, and can, thus, be controlled (during manufacture) by moving the push-rod 1002 to the desired axial position. The preloading force creates a seal between the diaphragm 204 and the push-rod 1002. Thus, to open the valve 1000, the pump pressure needs to break this seal, i.e., overcome the preloading force from the push-rod 1002 in addition to the stiction of the diaphragm slit. Consequently, the push-rod increases the cracking pressure, compared with that of, e.g., the valve 200 shown in FIGS. 2A and 2B, which has a planar slitted diaphragm.

Figure 10C:
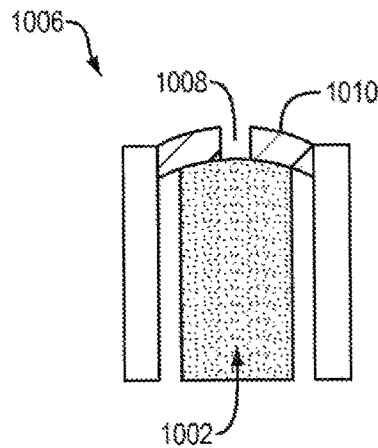
FIG. 10C is a side view of an alternative valve structure with a push-rod and an opening (instead of a slit) in the diaphragm in accordance with various embodiments.

In some push-rod embodiments, shown in FIG. 10C, the valve 1006 has, instead of a slit, a permanent opening 1008 in the diaphragm 1010 such that only the pre-loading force from the push-rod 1002 holds the valve sealed before forward pressure is applied. Stiction forces are eliminated from this valve, and once the forward pressure reaches the pre-loading force of the push-rod 1002, the valve opens and allows drug to flow therethrough. Since stiction forces are generally less reliable than pre-loading forces, this valve structure is advantageous when very accurate cracking forces are desired.

Figure 11A:
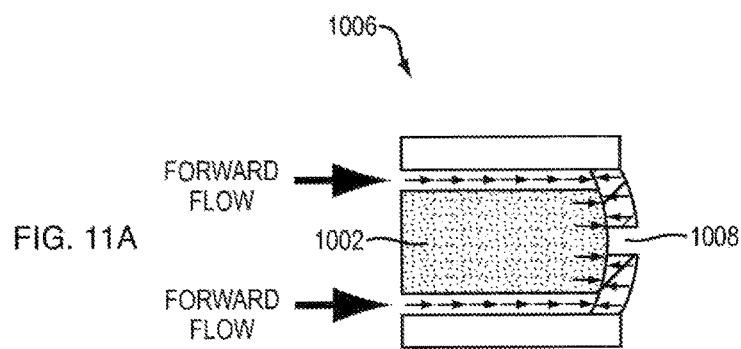
FIGS. 11A-11D illustrate the operation of the valve structure of FIG. 10B.
Figure 11B:
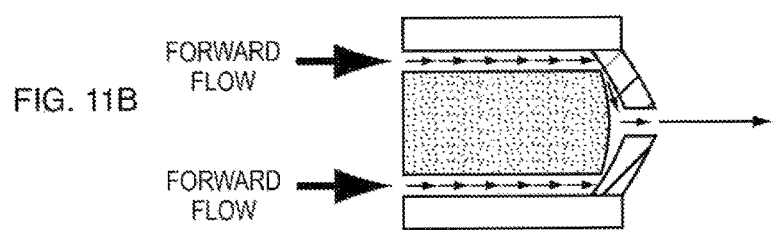
Figure 11C:
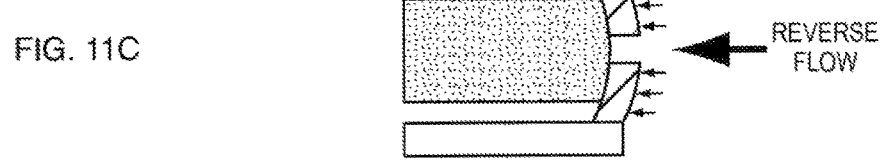
Figure 11D:
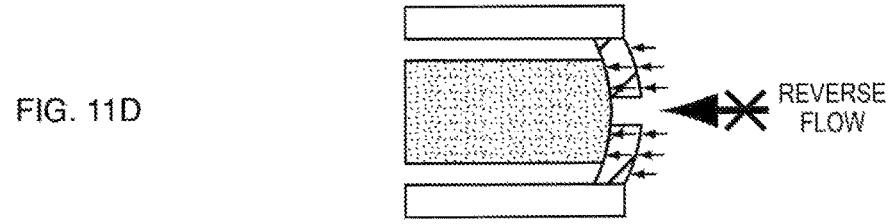

The working principle for the valve 1006 is illustrated in FIGS. 11A-11D. When forward pressure reaches the pre-loading force of the push-rod 1002, the valve 1006 opens (FIG. 11A) and allows drug to flow around the push-rod 1002 through the valve opening 1008 (FIG. 11B). However, when backpressure is applied, the push-rod 1002 plays a similar role as the backward-leakage stopper discussed above and prevents back flow by sealing of the diaphragm 1010 against the push-rod surface (FIGS. 11C and 11D). A similar sealing effect under backpressure is achieved in push-rod valves with slitted diaphragms (as shown in FIG. 10A). To ensure a good seal between the valve diaphragm and the push-rod, the push-rod preferably has a very smooth front surface shaped with constant or continuously and slowly varying curvature. The front surface of the push-rod may be shaped, e.g., like a hemisphere, hemi-ellipsoid, or hemi-paraboloid, etc. Acceptable degrees of surface roughness and/or bumpiness of the push-rod are generally a function of tolerable leakage levels. For a leakage limit of 0.5 nl/min, for instance, the roughness generally ought to be below 16 microinches.

3. Manufacturing Techniques

Figure 12A:
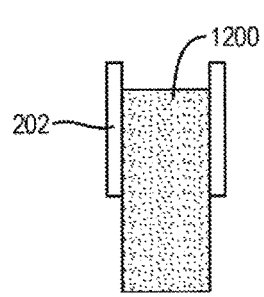
FIGS. 12A-12G and 13A-13G illustrate methods for creating the valve of FIGS. 2A and 2B by molding a diaphragm into the valve tube in accordance with various embodiments.
Figure 12B:
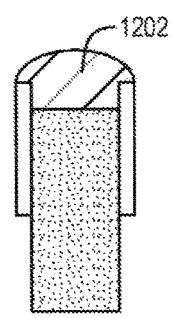
Figure 12C:
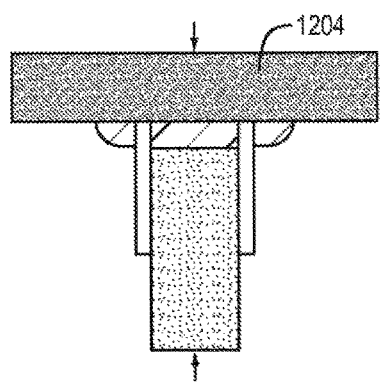
Figure 12D:
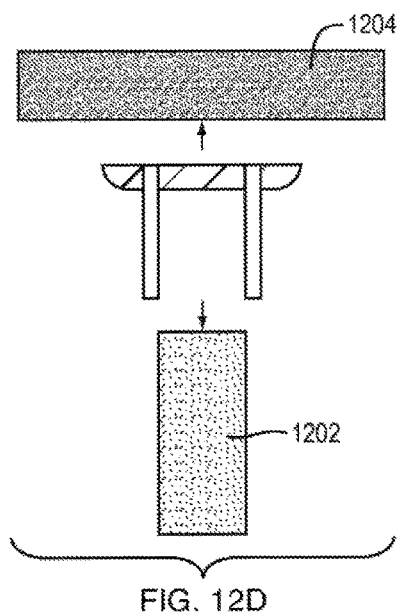
Figure 12E:
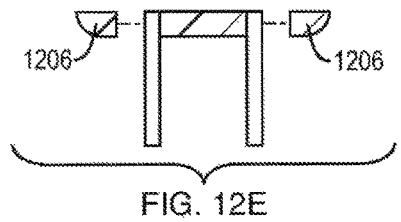
Figure 12F:
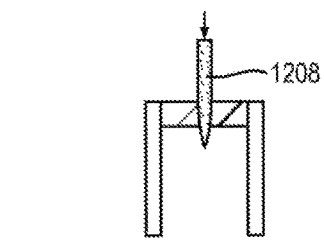
Figure 12G:
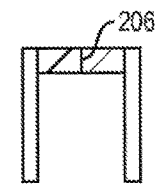

The microscale valves described above can be manufactured using any of a variety of approaches. For example, the elastomer diaphragm may be molded into a rigid tube. In one embodiment, illustrated in FIGS. 12A-12G, a rod 1200 with a diameter matching the inner diameter of the rigid tube is placed inside the tube 202, leaving a small space for the diaphragm material at the outlet end of the tube (FIG. 12A). The rod 1200 may be made, for instance, of metal (e.g., stainless steel, brass, copper, aluminum, gold, silver, platinum, etc.), plastic (e.g., polystyrene, polypropylene, polycarbonate, PEEK, etc.), glass (e.g., fused silica, soda lime, quartz, etc.), or a combination thereof. The rigid tube 202 may be made of glass, hard plastic (e.g., PEEK, polycarbonate, acrylic, etc.), or metal and may (but need not necessarily) be pre-treated with an adhesion promoter to increase the bonding strength for attachment of the elastomer diaphragm to the interior surface of the rigid tube. Following placement of the rod 1200 in the tube 202, a liquid-elastomer precursor 1202 is filled into the small space in front of the rod 1200 (FIG. 12B); examples of suitable elastomeric materials include silicone (such as LSR, HCE, LCE, etc.), synthetic rubber (such as EPDM, Butyl, Buna, etc.), and natural rubber. Then, a flat mold piece 1204 (e.g., of glass, hard plastic, or metal) is placed against the outlet end of the rigid tube 202, displacing any excess precursor (FIG. 12C). The elastomer precursor is thereafter cured under conditions readily ascertainable by persons of skill in the art, typically following manufacturer cure guidelines for the elastomer selected; the mold piece 1204 and rod 1200 are removed (FIG. 12D); and excess silicone 1206 is trimmed off the exterior of the tube 202 using a sharp blade 1208 (such as, e.g., an ophthalmic blade, razor blade, X-ACTO knife, scalpel blade, etc.) (FIG. 12E). The cured diaphragm 204 is then pierced using a small, sharp tool such as a fine wire, a fine needle, an electrical probe, an ophthalmic blade, etc. (FIG. 12F) to create the valve slit 206 (FIG. 12G).

Figure 13A:
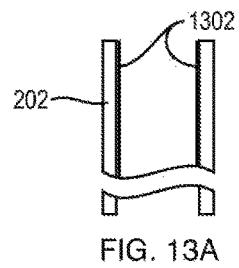
Figure 13B:
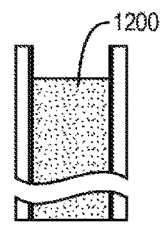
Figure 13C:
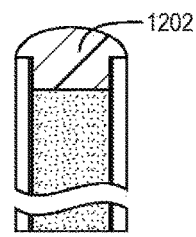
Figure 13D:
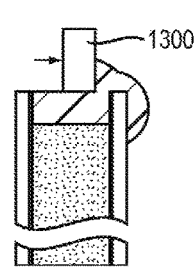
Figure 13E:
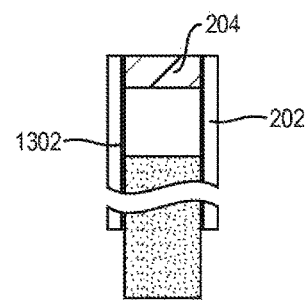
Figure 13F:
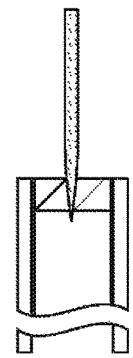
Figure 13G:
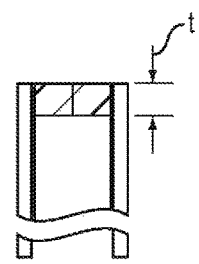

FIGS. 13A-13G illustrate a slightly modified method, in which, following filling of liquid elastomer precursor into the space created above the rod 1200 (FIG. 13C), excess precursor is removed using a squeegee 1300, i.e., a tool with a soft, smooth rubber blade that takes the excess precursor with it as it is pulled or pushed across the top rim and/or the outer surface of the rigid tube 202 (FIG. 13D). The elastomer is thereafter cured (FIG. 13E) and slitted (FIG. 13F). FIGS. 13A-13G also show a layer 1302 of adhesion promoter coated onto the interior surface of the rigid tube 202 to enhance the bonding strength between the elastomer diaphragm 204 and the tube 202.

Figure 14A:
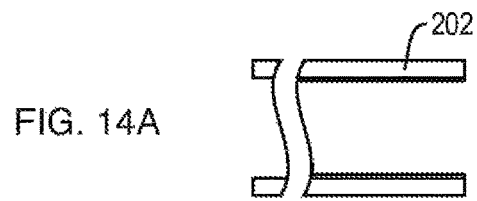
FIGS. 14A-14F illustrate a method for creating the valve of FIGS. 2A and 2B by affixing a pre-molded diaphragm into the valve tube in accordance with various embodiments.
Figure 14B:
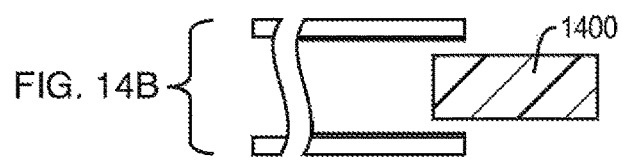
Figure 14C:
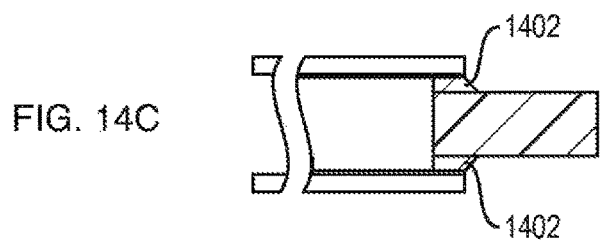
Figure 14D:
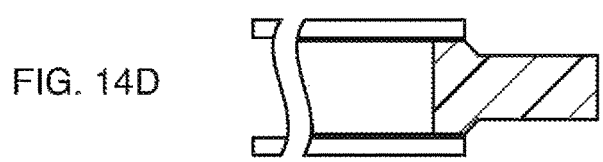
Figure 14E:
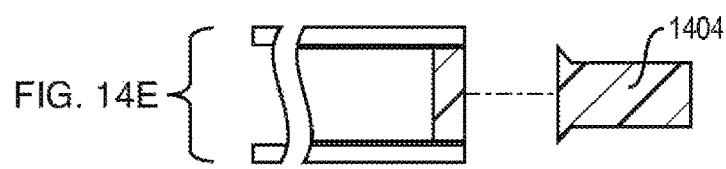
Figure 14F:
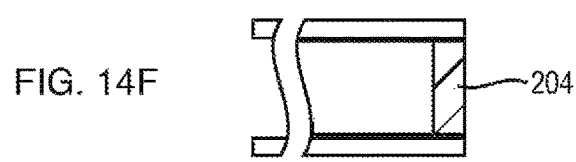

In yet another embodiment, illustrated in FIGS. 14A-14F, the diaphragm 204 is pre-molded and glued into the rigid tube 202. Practically, this can involve pre-molding a longer elastomer column 1400, e.g., in a microscale capillary tube (such as a glass micropipette, metal micropipette, or plastic micropipette), and inserting the molded elastomer column 1400 into the rigid tube 202 to a depth corresponding to the desired diaphragm thickness (FIG. 14B). Glue 1402 (e.g., silicone adhesive, epoxy, acrylic adhesive, etc.) may be applied between the mating surface portions of the elastomer column 1400 and the rigid tube 202 (FIG. 14C). Again, the rigid tube may be pre-treated with adhesion promoter (see FIG. 14A) to increase the bonding strength for the glue 1402. After the glue is cured (FIG. 14D), the portion 1404 of the elastomer column overhanging the rigid tube 202 may be cut off using a sharp cutting tool (FIG. 14E). The diaphragm may then be pierced to create the valve slit, as described above.

Figure 15A:
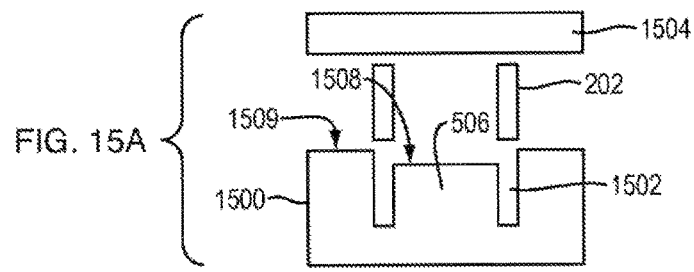
FIGS. 15A-15F illustrate a method for creating the valve of FIGS. 2A and 2B by injection molding in accordance with various embodiments.
Figure 15B:
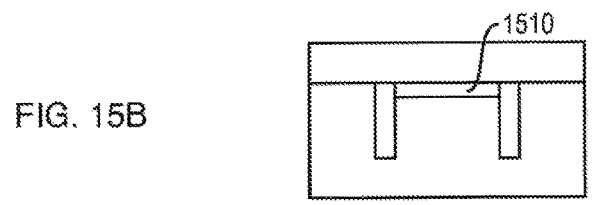
Figure 15C:
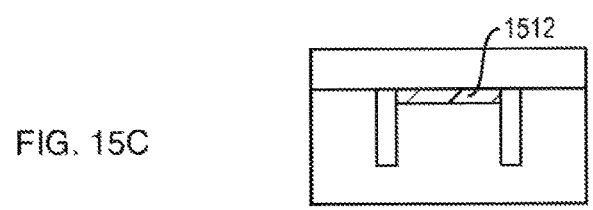
Figure 15D:
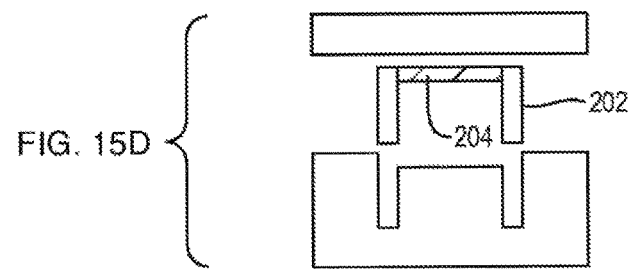
Figure 15E:
Figure 15F:
Figure 17A:
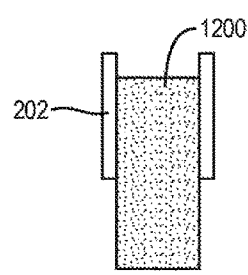
FIGS. 17A-17G illustrate a method for creating the valve of FIGS. 4A and 4B by molding a diaphragm with a bump into the valve tube in accordance with various embodiments.
Figure 17B:
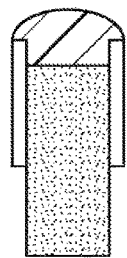
Figure 17C:
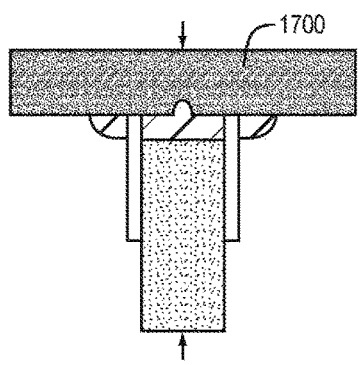
Figure 17D:
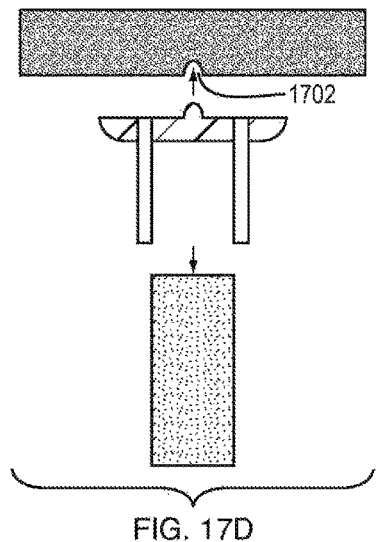
Figure 17E:
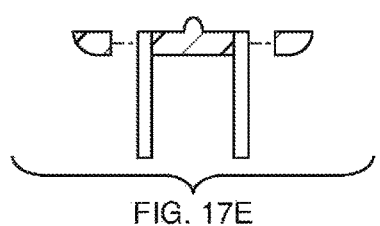
Figure 17F:
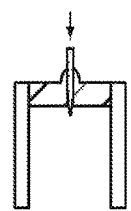
Figure 17G:
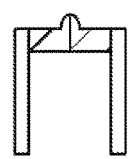
Figure 18A:
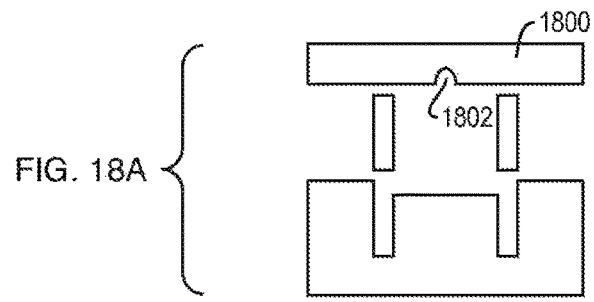
FIGS. 18A-18F illustrate a method for creating the valve of FIGS. 4A and 4B by injection-molding a diaphragm with a bump in accordance with various embodiments.
Figure 18B:
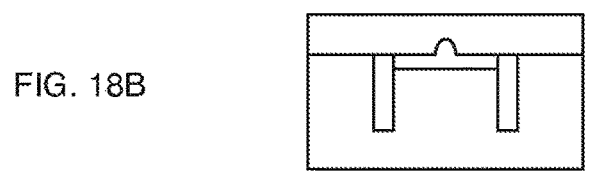
Figure 18C:
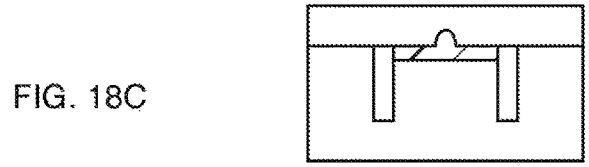
Figure 18D:
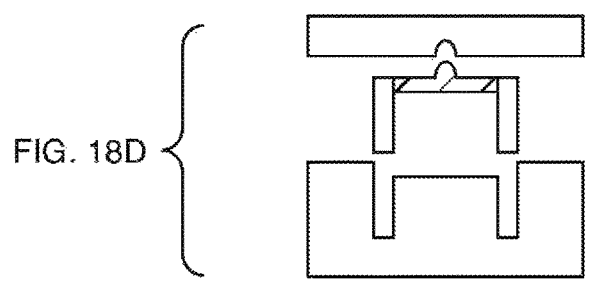
Figure 18E:
Figure 18F:

In another embodiment, injection molding is used to create the elastomer diaphragm 204 in the rigid valve tube 202, as shown in FIGS. 15A-15F. The mold is typically formed of a metal, such as aluminum or stainless steel, and may include two parts, as shown in FIG. 15A: a bottom mold part 1500 that has a groove 1502 complementary to and receiving the rigid valve tube 202, and a flat top mold part 1504. A center column 1506 defined in the bottom part 1500 by the groove 1502 has a top surface 1508 slightly below the top surface 1509 of the bottom part 1500 such that, when the top mold part 1504 is mounted on the bottom mold part 1500, a shallow cavity 1510 remains (FIG. 15B). The diaphragm is formed within this cavity 1510 by injection of liquid elastomer (FIG. 15C); for this purpose, the top part 1504 and/or the bottom part 1502 may include one or more bores connecting the mold exterior to the cavity 1510. The injected elastomer 1512 is cured in the injection mold under heat, typically by baking it in an oven. For multi-cavity molds, the mold is usually also pressurized. Additionally, a vacuum may be applied after injection, but prior to baking, to minimize any gas trapped within the liquid elastomer. After curing, the mold is opened and the valve structure including the rigid tube 202 and diaphragm 204 is removed therefrom (FIG. 15D). The valve may then be completed by creating a slit in the diaphragm (FIG. 15E) as described above.

Alternatively, the elastomer-diaphragm valve may be created using a micromachining-molding technique. In a micromachining-molding process, illustrated in FIGS. 16A-16I, two silicon wafers 1600, 1602 may be fabricated prior to the molding steps. The top wafer 1600 may include the walls of the valve tube 202 and tube-supporting structures 1604, and the bottom wafer 1602 may include a post 1606 whose top surface defines the bottom (i.e., upstream) surface of the diaphragm 204. Micro-etching may be employed to carve material out of the silicon wafers to generate the vertical sidewall profile of the tube 202 and supporting structures 1604 and the post 1606. The etching process may utilize any of several etching techniques well-known to those of skill in the art, including, e.g., deep reactive ion etching (DRIE), reactive ion etching (RIE), LIGA (lithography, electroplating, and molding), laser micromachining, etc. Following fabrication, the top and bottom wafers 1600, 1602 are aligned and assembled (FIG. 16B). Then, liquid-phase elastomer precursor 1608 is poured on top of the wafer assembly, filling the space within and surrounding the valve tube 202 (FIG. 16C). A vacuum may be applied to prevent bubbles from being trapped in the liquid elastomer during this filling step. The excess elastomer may then be squeegeed off (FIG. 16D) or otherwise removed. After curing (FIG. 16E), the bottom mold is removed (FIG. 16F), and the valve is gently detached from the top wafer by breaking or cutting the top wafer at the bottom end of the groove (FIG. 16G). Finally, the molded diaphragm is pierced with a sharp tool to create the valve slit (FIG. 16H). The micromachining-molding approach is amenable to simultaneous manufacture of multiple valve structures with top and bottom wafers 1600, 1602 that include the valve tube walls, tube-supporting structures 1604, and posts 1606 for multiple valves. Further, this approach, like the injection-molding technique described with respect to FIGS. 15A-15F, facilitates reproducible valve manufacture by repetitive use of the same mold parts or wafers.

Figure 19A:
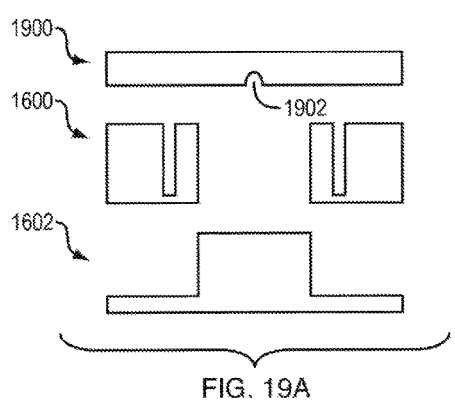
FIGS. 19A-19H illustrate a method for creating the valve of FIGS. 4A and 4B by micromachining a mold with a bump recess and the molding the diaphragm in accordance with various embodiments.
Figure 19E:
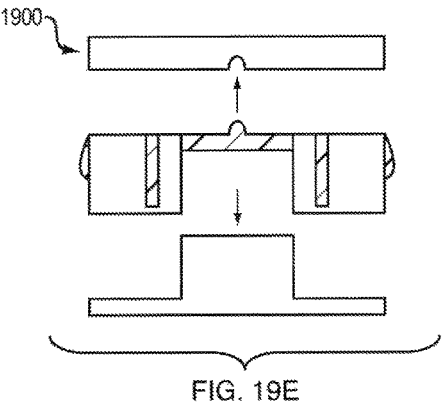
Figure 19B:
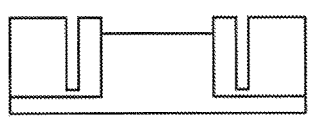
Figure 19C:
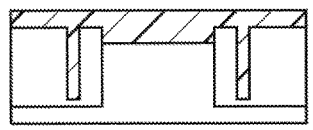
Figure 19D:
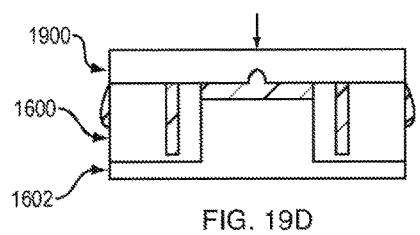
Figure 19F:
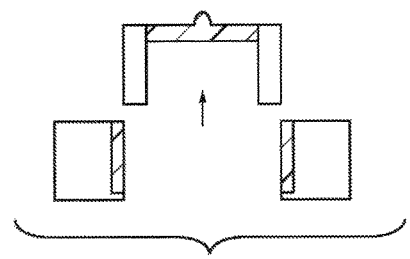
Figure 19G:
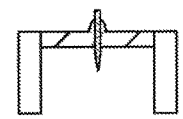
Figure 19H:
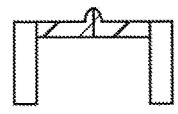

As discussed above, in certain embodiments, a small bump is molded into the valve diaphragm to increase the back-flow resistance (i.e., the breakdown pressure) of the valve. The molding method described in FIGS. 12A-12G can be straightforwardly modified to create such a bump, as shown in FIGS. 17A-17G: following insertion of the rod 1200 in the valve tube 202 and filling of a small space thereabove with liquid elastomer precursor, a front mold 1700 that includes a recess 1702 complementary in shape to the bump (i.e., a "negative bump"), but is otherwise flat, is placed against the tube 202 to displace excess precursor. Curing of the precursor in the presence of the front mold 1700 forms a diaphragm with the desired bump. Alternatively, the bump may be created by modifying the injection-molding technique depicted in FIGS. 15A-15E. As shown in FIGS. 18A-18F, the otherwise flat top mold part 1800 may simply be provided with a "negative-bump" recess 1802 that results, after curing of the precursor, in the desired bump in the middle of the diaphragm. In yet another embodiment, the micromachining-molding approach illustrated in FIGS. 16A-16I is adapted to create the bump. As shown FIGS. 19A-19H, the adapted technique utilizes three silicon-wafer mold pieces: in addition to the wafer 1600 that includes the valve tubes and supporting structures (now the middle one of the wafers) and the bottom wafer 1602 that includes a post defining the upstream surface of the diaphragm, a third, top wafer 1900 with a "negative-bump" recess 1902 in its otherwise flat underside is provided. Like the vertical profile in the bottom and middle wafers, the recess 1902 in the top wafer 1900 can be etched into the silicon wafer, e.g., using wet etching (with KOH, EDP, TMAH, etc.), plasma etching (with oxygen, SF6, CF4, etc.), or other conventional silicon etching techniques. Following fabrication of the wafers 1600, 1602, 1900, the middle and bottom wafers 1600, 1602 are aligned and assembled, and liquid-phase elastomer precursor is poured on top of this assembly. The patterned top wafer 1900 is then aligned and gently assembled with the middle and bottom wafer assembly, expelling excess elastomer while creating the bump (FIG. 19D). After curing, the assembly is opened and the top and bottom wafers 1900, 1602 are removed (FIG. 19E), and the valve is gently detached from the middle wafer 1600. However the bump is created, the cured diaphragm is pierced in the location of the bump to form the valve slit 206.

Figure 20A:
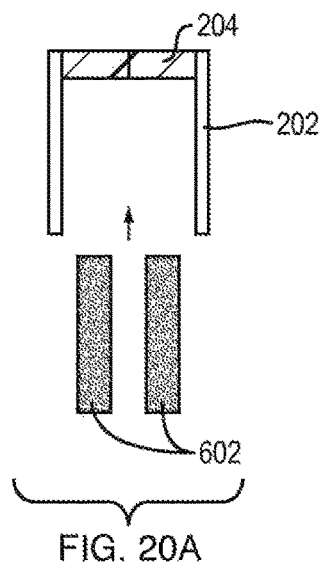
Figure 20B:
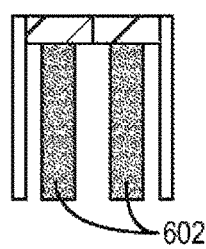
Figure 20C:
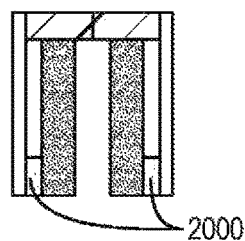

As described above, various valve embodiments include an anti-bending structure (backward-leakage stopper) to improve the valve back-flow resistance. This stopper can be manufactured by conventional techniques (e.g., by cutting a tube segment 602 of the appropriate length from a prefabricated tube of suitable inner and outer diameters, or by molding or machining a more complex stopper structure 604), and thereafter assembled with a elastomer-diaphragm valve structure fabricated by any of the methods described above. With reference to FIGS. 20A-20C, to install the stopper tube 602, it is slowly inserted into the rigid valve tube 202 until it gently touches the diaphragm 204 (FIG. 20A). Then, the stopper tube 602 is affixed to the outer valve tube 202 by, for instance, chemical adhesion (using, e.g., epoxy 2000, silicone, acrylic, etc.) (as shown in FIG. 20B), mechanical connection (e.g., crimping, screws, forming, a spring-loaded mechanism, etc.), or an advanced bonding technique (such as ultrasonic bonding, RF bonding, thermal resistive bonding, etc.); these and other suitable methods for permanently attaching the stopper 602 to the valve tube are well-known to those of skill in the art. In embodiments that employ a stopper 604 integrated into upstream tubing, as shown in FIG. 6B, the same bonding techniques may be used to attach the valve exterior to the interior surface of the tubing such that the stopper 604 comes to abut the diaphragm 204.

When a backward-leakage stopper tube 602 is used, air can be trapped in the gap between the stopper 602 and the surrounding rigid valve tube 202; eliminating such trapped air is one of the challenges arising from the use of a stopper 602, and can be accomplished in different ways. In one approach, illustrated in FIGS. 21A-21G, the rigid valve tube 202 is filled with liquid elastomer precursor 2100 to a depth far exceeding the intended thickness of the diaphragm 204 (e.g., to more than half of its length) (FIG. 21A). A tubular mold piece 2102 complementary in shape to the valve tube 202, but having an outer diameter that is slightly smaller than the inner diameter of the valve tube 202, is then inserted into the valve tube 202 (FIG. 21B), displacing a large fraction of the elastomer precursor while filling the gap between the mold piece 2102 and the valve tube 202 from the diaphragm down to a certain distance (upstream thereof); after the elastomer has been cured, the portion filling the gap forms a skirting 208 integral with the diaphragm 204. The mold piece 2102 may then be removed (FIG. 21C), and a valve slit 206 be cut into the diaphragm 204 (FIG. 21D). Thereafter, the stopper 602 may be inserted into the space defined by the elastomer skirt (FIG. 21E), and any of the bonding techniques previously mentioned may be used to bond the stopper 602 and valve tube 202 together.

An alternative technique, which is illustrated in FIGS. 22A-22G, involves forcing the liquid elastomer precursor into a rigid valve tube with the mold piece 2102 pre-installed (FIGS. 22A and 22B). When the precursor fills the desired length of the gap between the mold 2102 and the valve tube 202, it is cured, and the mold 2102 is thereafter removed (FIG. 22C). As in FIG. 21D, the stopper may then be inserted into the space defined by the newly formed elastomer membrane and skirt, and bonded to the valve tube 202 using any suitable bonding technique.

As described above, certain valves in accordance herewith include a push-rod, placed inside the valve at a precisely determined axial location and thereby pre-bending the diaphragm by a certain amount, to achieve a more reliable cracking pressure. This type of valve may be created by, first, molding or otherwise installing the valve diaphragm 204 in the rigid valve tube 202 in any manner described above, cutting or piercing the diaphragm 204 to create a slit 206 or permanent opening 1008 therein, and then inserting the push-rod 1002 slowly and carefully into the rigid valve tube 202, as illustrated in FIGS. 23A-23C for a slitted diaphragm and FIGS. 23D-23F for a diaphragm with an opening 1008, respectively. Insertion of the push-rod 1002 may be facilitated by suitable fixture with a microscale manipulator for precise displacement control; once the push-rod comes in contact with the diaphragm 204, the micromanipulator is operated to displace the diaphragm 204 to the desired degree of deflection (FIGS. 23B and 23E). For a specified desired cracking pressure, the requisite deflection may be calculated analytically or numerically (e.g., using finite element analysis). Alternatively or additionally, the deflection may be determined through load-deflection experiments with diaphragms having similar dimensions and geometries. Once the determined deflection is reached, the push-rod is fixed to the outer tube (FIGS. 23C and 23F), e.g., using a traditional bonding technique the employs an adhesive 2300, a mechanical connection technique, or an advanced bonding technique.

Figure 24A:
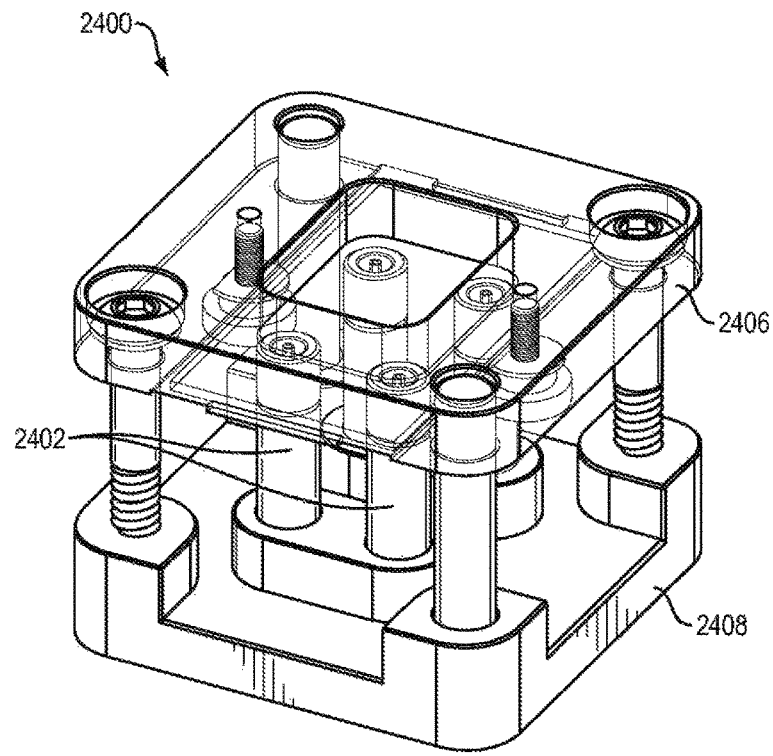
FIG. 24A is a transparent perspective view.
Figure 24B:
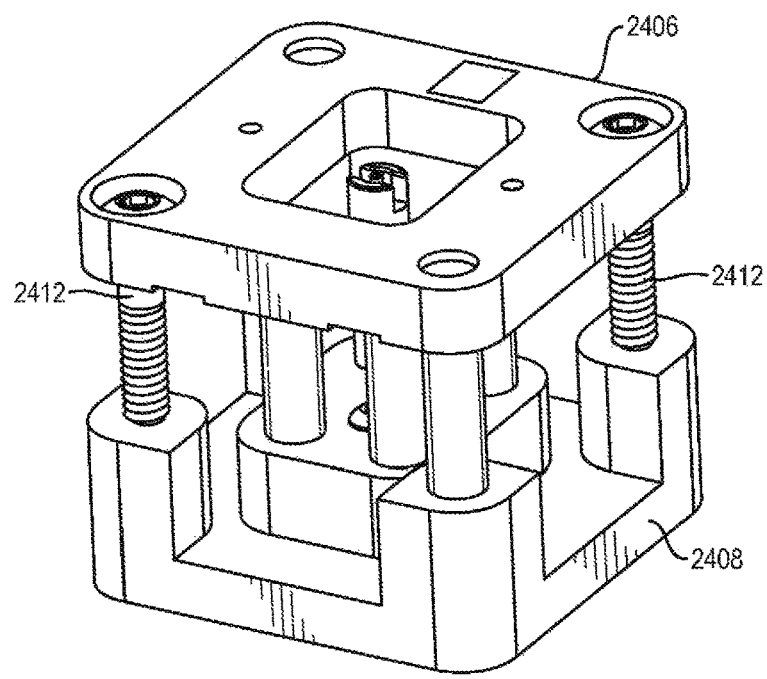
FIGS. 24B-24D are partial opaque views, of a stack mold for manufacturing valve structures in accordance with various embodiments.
Figure 24C:
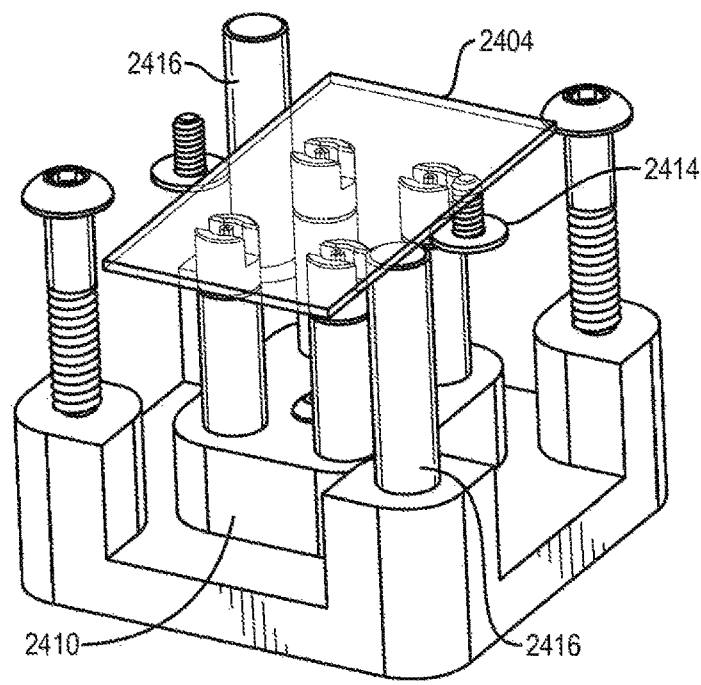
Figure 24D:
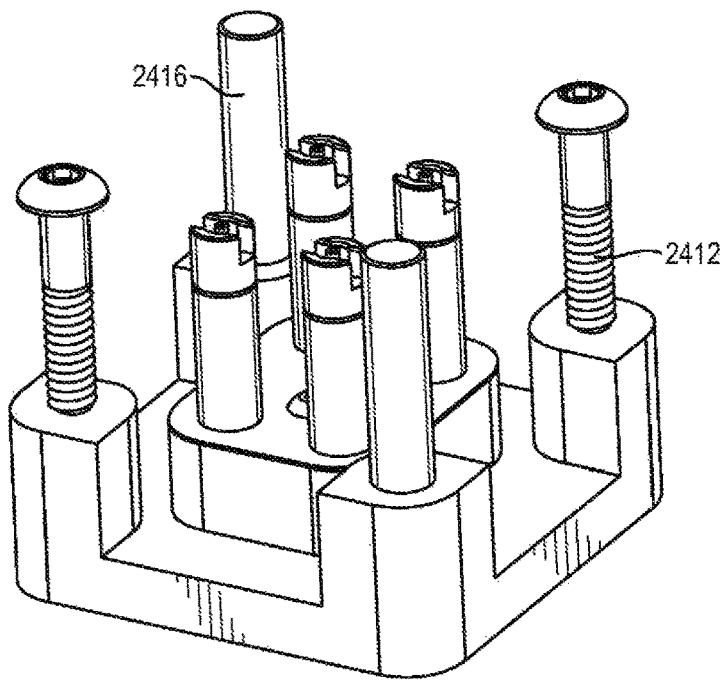
Figure 24E:
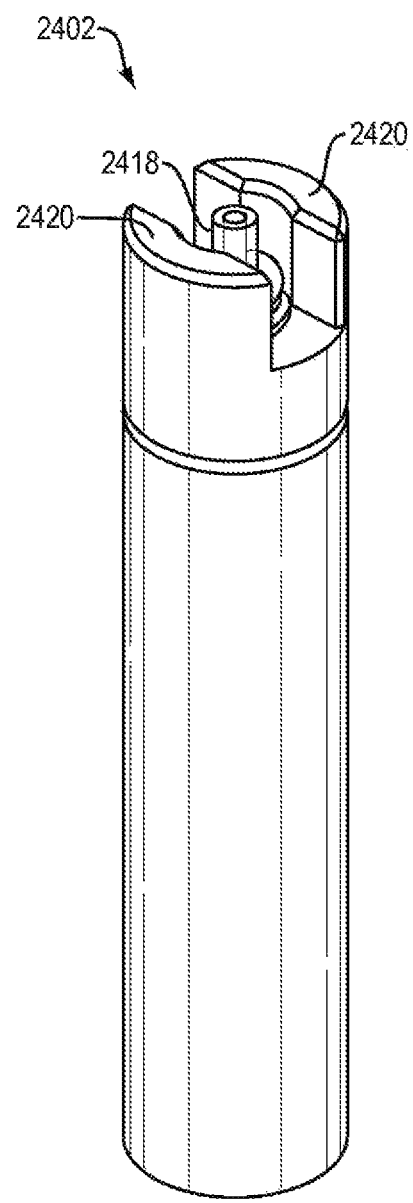
FIG. 24E is an enlarged view of a mold column including the functional pin of the stack mold of FIGS. 24A-24D.

In yet another alternative manufacturing method, a stack mold fixture is used to produce valves at greater quantities and lower cost while increasing reproducibility. This fixture may achieve, in particular, a consistent thicknesses across the diaphragm and skirt sections. Additionally, the resulting valve structures require only minimal (if any) post-fabrication trimming. An exemplary stack mold fixture is illustrated in FIG. 24A and FIGS. 24B-24D in transparent view and various partial views, respectively. The stack mold fixture 2400 includes four mold columns 2402 (one of which is separately depicted in FIG. 24E) and a flat slide 2404 or similar flat member (shown in FIG. 24C) for placement thereon, as well as parallel top and base bracket members 2406, 2408 that serve to secure the columns 2402 and slide 2404 therebetween. The mold columns 2402 may, for instance, be fixedly mounted on the base bracket 2408, e.g., via an elevated base-bracket portion 2410, and the top bracket 2406 may be reversibly affixed to the base bracket 2408 with screws 2412, clamps, or other mechanical means. When the mold fixture 2400 is fully assembled, the flat slide 2404 is clamped between the top surface of the mold columns 2406 and the bottom surface of the top bracket 2406; it may be further secured to the top bracket via screws 2414. The top and base brackets 2406, 2408 are spaced, in the assembled state, by a distance corresponding to the height of the mold columns 2402 plus the thickness of the slide 2404, and/or corresponding to the height of any support rods 2416.

Each of the mold columns 2402 includes a pin 2418 that may be partially surrounded, along a circle concentric with the pin 2418, by one or more spacers 2420; gaps in the arrangements of spacers 2420 facilitate access to the pin 2418 when the stack mold fixture 2400 is closed. The pins 2418 constitute the basic functional components of the stack mold fixture 2400, i.e., they serve as molds for the valve structures. A separate valve is created with each pin 2418; thus, the number of pins 2418 determines the number of valves that can be produced simultaneously with the stack mold fixture 2400. As shown in FIGS. 25A-25E, which illustrate valve manufacture using the pin-and-spacer configuration, the pin 2418 has two tiers: a first tier 2501 whose diameter matches the inner diameter of the valve tube, and a second tier 2502 whose diameter matches the inner diameter of the diaphragm valve, which is measured between opposing points at the inner surface of the skirt. (In other words, the inner diaphragm diameter equals the outer diaphragm diameter less twice the thickness of the skirt). When, during manufacture, a valve tube 202 is placed over the pin 2418, the first tier 2501 serves to hold the tube 202 in place via contact between the interior tube surface and the pin, whereas the second, narrower tier 2502 leaves space between the pin and the inner tube surface for forming the diaphragm skirt. The two tiers 2501, 2502 are typically arranged concentrically around a common axis such that the space between the pin 2418 and the inner surface of the tube 202 is of uniform thickness. The first tier 2501 may include one or more exit flow channels 2503 through which gas and excess liquid elastomer precursor 1202 can flow out. In certain embodiments, the amount of liquid elastomer precursor applied is carefully adjusted to create a specified skirt length, such that no or only minimal precursor flows out. The spacer(s) 2420 that circumferentially and partially surround the pin 2418 extend in height beyond the second tier 2502. Thus, when the flat slide 2404 is placed on top of the spacer(s) 2520, it forms a void between the top surface of the pin 2418 and the top surface of the spacer(s) 2520. The height of that void, i.e., the height difference between the top surfaces of the spacer(s) 2520 and the pin 2418, is equal to the thickness of the diaphragm created in the stack mold fixture 2400. Alternatively, spacer structures may be placed remotely from the pins to improve access to the pin for removing excess elastomer precursor.

Figure 25A:
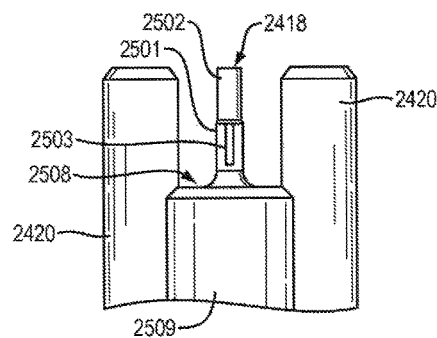
FIGS. 25A-25E illustrate a method for creating a valve in accordance with various embodiments using the stack mold of FIGS. 24A-24E.
Figure 25D:
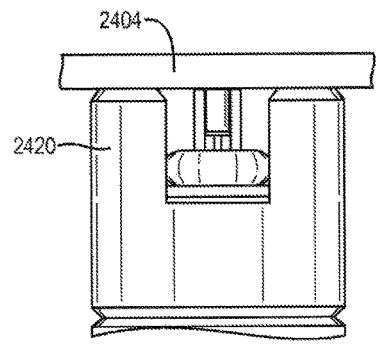
Figure 25B:
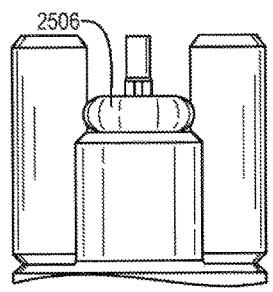

Accordingly, to create a valve structure, a valve tube 202 of suitable length and having an inner diameter matching the diameter of the first pin tier 2501 is placed over the pin 2418. The valve tube 202 may rest on top of an O-ring 2506 placed over the pin 2428 and resting on the support surface 2508 from which the pin 2418 extends (i.e., the top surface of the bottom fillet section 2509 of the mold column 2402), as shown in FIG. 25B. The O-ring 2506 generally serves to compensate for small differences between the actual and nominal lengths of the valve tube 202, and thus accommodates tight tolerance in the resulting valve structures despite difficulties in precisely manufacturing the valve tube 202. Compression and counter-acting forces provided by the O-rings 2506 on the various mold columns 2402 enable keeping tubes 202 with minute height differences all pressed against the flat slide 2404.

Then, the rigid tube 202 is filled with liquid elastomer precursor. Alternatively, the rigid tube 202 may be filled with liquid elastomer precursor prior to being mounted on the pin 2418; in that case, elastomer precursor is displaced from the interior space of the tube 202 and squeezed through the exit flow channels 2503 as the tube 202 is being mounted. Additional liquid-elastomer precursor may be added as necessary to the top of the tube 202. The flat, smooth slide 2404 may then be placed to rest on the spacer(s) 2504, as illustrated in FIG. 25D; thereby, an elastomer layer of uniform thickness is formed between the top surface of the pin 2418 and the bottom surface of the slide 2404. In the process, any excess liquid elastomer precursor is forced from the interior of the tube 202 through the exit flow channels 2503 and/or between the flat slide 2404 and rigid tube 202. This excess liquid elastomer precursor may be manually removed at this point, by access through openings between or around the spacer(s), to minimize post-fabrication trimming. In embodiments where a small bump is molded into the valve diaphragm to increase the back-flow resistance, the smooth slide 2404 is etched to create a recess complementary in shape to the desired bump. Further, the smooth slide 2404 may be coated with different materials to reduce adhesion of the liquid elastomer, thereby making the removal of the diaphragm easier; suitable adhesion-inhibiting coatings include, but are not limited to, parylene and sputtered gold.

Figure 25E:
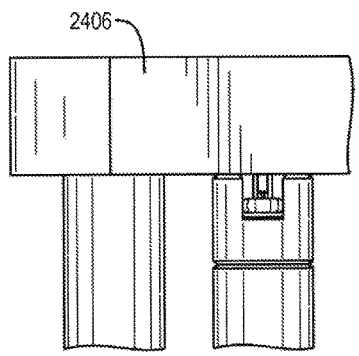
Figure 25C:
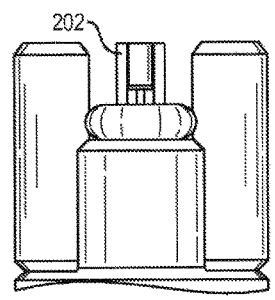

To avoid relative movement between the slide 2404 and the mold columns 2402, the top bracket member 2406 may be placed on top of the flat slide 2404 (as shown in FIG. 25E) and secured to the base bracket member 2408. Alternatively, the flat slide 2404 may be secured to the top bracket member 2406 before placement and securing to the base bracket member 2408. The elastomer is then cured by baking or other appropriate means according to manufacturer cure guidelines, which may be specific to the selected type of elastomer. Following curing, the top bracket member 2406 is removed, and the rigid tube 202, along with the diaphragm 204 molded thereto, is extracted. Finally, the molded diaphragm 204 is pierced with a sharp tool to create the desired valve slit or opening, as described above with respect to other manufacturing methods. In embodiments including a push-rod or backward-leakage stopper, the prefabricated rod or stopper may be inserted into the valve structure.

Of course, the stack mold fixture and method of use thereof can be modified in many ways, as will be readily apparent to those of skill in the art. Possible variant configurations of the stack mold fixture include, for example, different numbers and/or placement of the mold columns 2402; different fastening features for securing the top and base bracket members 2406, 2408; entirely different bracket structures or means for keeping the flat slide in place; different spacer configurations (e.g., a single large spacer in the center region of the stack mold that allows for greater access to the all pins 2418); and/or different geometries of the bottom fillet sections 2509 of the mold columns 2402. Further, instead of using a flat slide 2404, a different structure with a flat underside may be used to create a diaphragm of uniform thickness, and the shape of the top bracket member 2406 may be adjusted accordingly to secure the structure. Alternatively, a different method for removing excess elastomer precursor to form the diaphragm may be employed; for instance, the precursor may be squeegeed away with a blade or a flat member that is slid across the spacer(s) 2420.

Various embodiments of the invention are described above. It will, however, be apparent to those of ordinary skill in the art that other embodiments incorporating the concepts disclosed herein may be used without departing from the spirit and scope of the invention. Accordingly, the above description is intended to be only illustrative and not restrictive.

What is claimed is:

1. An in-line check valve comprising:
   a first tube defining a first lumen for flow of fluid therethrough;
   affixed to an interior surface of the first tube and spanning a cross-section thereof, an elastic diaphragm comprising a slit or opening therethrough; and
   a backward-leakage stopper (i) comprising a second lumen therethrough, (ii) extending beyond and surrounding an inlet end of the first tube, (iii) affixed to an exterior surface of the first tube, and (iv) abutting the diaphragm at a first side thereof;
   wherein the second lumen is centered at the slit or opening and the valve is configured to (i) open upon application of at least a cracking pressure on the first side of the diaphragm so as to permit fluid to pass through the slit or opening from the first side to a second side of the diaphragm, and (ii) prevent backflow of fluid from the second side to the first side until at least a breakdown pressure is reached on the second side.

2. The check valve of claim 1, wherein a diameter of the first tube is less than 1 mm.

3. The check valve of claim 1, wherein a largest dimension of the valve is less than 1 mm.

4. The check valve of claim 1, wherein the elastic diaphragm extends into a skirt secured to the interior surface of the first tube.

5. The check valve of claim 4, wherein the first tube includes holes through a side wall thereof in regions adjacent the skirt.

6. The check valve of claim 5, wherein the skirt is secured to the first tube by epoxy extending through the holes.

7. The check valve of claim 1, wherein the diaphragm comprises a convex bump on the first side, the slit or opening being co-located with the bump.

8. The check valve of claim 1, wherein the slit or opening is configured to flex and open upon application of at least the cracking pressure on the first side of the diaphragm.

9. The check valve of claim 1, wherein the second lumen is sized to impose a specified restriction on a rate of fluid flow therethrough.

10. The check valve of claim 1, wherein the stopper further comprises:
    a pre-load member urged against the first side of the diaphragm so as to flex the diaphragm and occlude the slit or opening in a closed state of the valve.

11. The check valve of claim 10, wherein the cracking pressure depends at least in part on an axial position of the pre-load member.

12. An in-line check valve comprising:
    a first tube defining a first lumen for flow of fluid therethrough;
    affixed to an interior surface of the first tube and spanning a cross-section thereof, an elastic diaphragm comprising a slit or opening therethrough; and
    a backward-leakage stopper (i) having multiple lumina therethrough, (ii) extending beyond and surrounding an inlet end of the first tube, (iii) affixed to an exterior surface of the first tube, and (iv) abutting the diaphragm at a first side thereof;
    wherein the valve is configured to (i) open upon application of at least a cracking pressure on the first side of the diaphragm so as to permit fluid to pass through the slit or opening from the first side to a second side of the diaphragm, and (ii) prevent backflow of fluid from the second side to the first side until at least a breakdown pressure is reached on the second side.

13. The check valve of claim 12, wherein a diameter of the first tube is less than 1 mm.

14. The check valve of claim 12, wherein a largest dimension of the valve is less than 1 mm.

15. The check valve of claim 12, wherein the elastic diaphragm extends into a skirt secured to the interior surface of the first tube.

16. The check valve of claim 15, wherein the first tube includes holes through a side wall thereof in regions adjacent the skirt.

17. The check valve of claim 16, wherein the skirt is secured to the first tube by epoxy extending through the holes.

18. The check valve of claim 12, wherein the diaphragm comprises a convex bump on the first side, the slit or opening being co-located with the bump.

19. The check valve of claim 12, wherein the slit or opening is configured to flex and open upon application of at least the cracking pressure on the first side of the diaphragm.

20. The check valve of claim 12, wherein at least one of the multiple lumina associated with the stopper is sized to impose a specified restriction on a rate of fluid flow therethrough.

21. The check valve of claim 12, wherein the stopper further comprises:
   a pre-load member urged against the first side of the diaphragm so as to flex the diaphragm and occlude the slit or opening in a closed state of the valve.

22. The check valve of claim 21, wherein the cracking pressure depends at least in part on an axial position of the pre-load member.

* * * * *